US009765069B2

(12) United States Patent
Moloney et al.

(10) Patent No.: US 9,765,069 B2
(45) Date of Patent: Sep. 19, 2017

(54) ANTIMICROBIAL COMPOUNDS

(71) Applicant: OXFORD UNIVERSITY INNOVATION LIMITED, Oxford (GB)

(72) Inventors: Mark Moloney, Oxford (GB); Yong-chu Jeong, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 14/410,538

(22) PCT Filed: Jun. 24, 2013

(86) PCT No.: PCT/GB2013/051657
§ 371 (c)(1),
(2) Date: Dec. 22, 2014

(87) PCT Pub. No.: WO2014/001775
PCT Pub. Date: Jan. 3, 2014

(65) Prior Publication Data
US 2015/0299187 A1    Oct. 22, 2015

(30) Foreign Application Priority Data

Jun. 25, 2012 (GB) .................................. 1211203.3

(51) Int. Cl.
| | |
|---|---|
| C07D 471/04 | (2006.01) |
| C07D 417/06 | (2006.01) |
| C07D 211/04 | (2006.01) |
| C07D 401/06 | (2006.01) |
| C07D 403/06 | (2006.01) |
| C07D 405/06 | (2006.01) |
| C07D 409/06 | (2006.01) |
| C07D 207/44 | (2006.01) |
| C07D 213/69 | (2006.01) |
| C07D 207/444 | (2006.01) |

(52) U.S. Cl.
CPC ......... *C07D 471/04* (2013.01); *C07D 207/44* (2013.01); *C07D 207/444* (2013.01); *C07D 211/04* (2013.01); *C07D 213/69* (2013.01); *C07D 401/06* (2013.01); *C07D 403/06* (2013.01); *C07D 405/06* (2013.01); *C07D 409/06* (2013.01); *C07D 417/06* (2013.01)

(58) Field of Classification Search
CPC .............. C07D 207/444; C07D 211/04; C07D 401/06; C07D 403/06; C07D 405/06; C07D 409/06; C07D 417/06; C07D 471/04
USPC .............. 514/299, 326, 328, 414, 422, 423; 546/183, 208, 209, 213, 220; 548/468, 548/517, 527, 540
See application file for complete search history.

(56) References Cited

U.S. PATENT DOCUMENTS 3,968,122 A    7/1976  Nazareth et al. ............. 548/403

FOREIGN PATENT DOCUMENTS

| EP | 1116715 | 7/2001 |
|---|---|---|
| WO | WO 2008014311 | 1/2008 |

OTHER PUBLICATIONS

Jeong et al. "Synthesis of and . . . " CA154:234348 (2011).*
PTO-237 for PCT/GB2013/05167 (2013).*
Barnickel et al. "3-functionalization . . . " CA157:437975 (2012) (available online 2010).*
Katzka "Synthesis of tetrmic . . . " dissertation, p. 1-151 (2006).*
Schlenk et al. "A selective 3- . . . " Chem. Eur. J 16, pp. 2599-2604 (2010).*
Spurring et al. "Preparation of new . . . " CA155:589124 (2011).*
International Search Report and Written Opinion for PCT/GB2013/051657, Aug. 22, 2013, 14 pages.
Jeong et al. "Synthesis of and Tautomerism in 3-Acyltetramic Acids", *J. Org. Chem.* 2011, 76, No. 5, pp. 1342-1354, Jan. 20, 2011.
Gavrielatos et al."Synthesis and NMR spectroscopic studies of novel N-acetyl-3-aminoalkyl tetramic acids", *Heterocyclic Communications* 1999, 5, 515-520.
Petroliagi et al. "Synthesis and enantiomeric excess measurements of optically active N-acetyl tetramic acids", *Tetrahedron Asymmetry* 1999, 10, 1873-1875, May 1, 1999.
Petroliagi et al. "An efficient synthesis of novel N-acetyl-3-alkanoyl and 3-dienoyl tetramic acids", *J. Chem. Soc., Perkin Trans.* 1, 1997, 23, 3543-3548, Jan. 1, 1997.
Barkley et al. "Synthesis, NMR spectroscopic and X-ray crystallographic studies of N-acetyl-3-butanoyltetramic acid", *J. Chem. Soc., Perkin Trans.* 2, 1994, 6, 1271-1274, Jan. 1, 1994.
Igglessi-Markopoulou et al. "The cyclization of the acetylaminoacetyl derivatives to [alpha]-substituted tetramic acids and the formation of N-acetyl-[alpha]-substituted tetramic acids", *J. Heterocyclic Chem.* 1985, 22, 1599-1606, Nov. 1, 1985.
Hurdle et al."Evaluation of Analogs of Reutericyclin as Prospective Candidates for Treatment of Staphylococcal Skin Infections", *Antimicrobial Agents and Chemotherapy* 2009, 53, 4028-4031, Sep. 1, 2009.
Hurdle et al"Reutericyclin and related analogues kill stationary phase Clostridium difficile at achievable colonic concentrations", *J. Antimicrob. Chemother.* 2011, 66, 1773-1776, May 31, 2011.
Sengoku et al., "A Synthetic Approach to Diverse 3-Acyltetramic Acids via O- to C-Acyl Rearrangement and Application to the Total Synthesis of Penicillenol Series" The Journal of Organic Chemistry, vol. 77, Issue 9, Apr. 17, 2012 pp. 4391-4401.

(Continued)

*Primary Examiner* — Noble Jarrell
(74) *Attorney, Agent, or Firm* — Squire Patton Boggs (US) LLP

(57) ABSTRACT

The present invention relates to certain tetramic acid derivatives that are suitable for use in the preparation and development of antimicrobial (e.g. antibacterial or antifungal) compositions. The present invention also relates to the use of such compounds as antimicrobial (e.g. antibacterial or antifungal agents) and, in particular, as topical antibacterial or antifungal agents.

16 Claims, No Drawings

(56) References Cited

OTHER PUBLICATIONS

Takahata et al., "Metallo-ketene-S,N-acetals. New Synthesis of Azacycloalka[3,2-c]pyridin-2-ones" Heterocycles, vol. 24, No. 5, 1986, pp. 1247-1248.

Wang et al., "Synthesis, characterization and biological activity of novel (5-RS,6-S)-5-sec-butyl-3-(1-substituted-amino)ethylidene-1H-pyrrolidine-2,4-diones" ARKIVOC, Apr. 20, 2010 pp. 31-48.

* cited by examiner

ANTIMICROBIAL COMPOUNDS

The present invention relates to certain tetramic acid derivatives that are suitable for use in the preparation and development of antimicrobial (e.g. antibacterial or antifungal) compositions. The present invention also relates to the use of such compounds as antimicrobial (e.g. antibacterial or antifungal agents) and, in particular, as topical antibacterial or antifungal agents.

As the use of antibiotics becomes increasingly widespread, antibiotic-resistant strains of bacteria have evolved. As a result, there is a growing need for new antibiotics to combat the continuous emergence of such resistant strains.

Natural products containing a tetramate nucleus are known and some of these compounds are known to exhibit antibacterial activity. For example, streptolydigin and tirandamycin are known to have antibacterial activity against Gram-positive and Gram-negative bacteria, while reutericyclin (Formula III below) is bacteriostatic or bactericidal to Gram-positive bacteria.

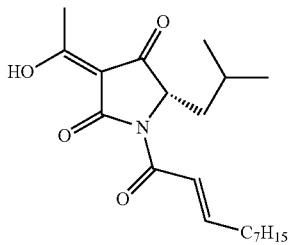

Magnesidin A (Formula IV below) is also known to have antibacterial activity

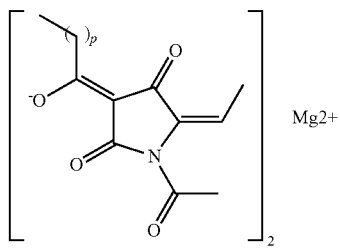

Attempts have been made to use such natural product as starting points to identify synthetic compound libraries of antibacterial agents. Attempts have also been made to use the tetramate nucleus as a scaffold for designing compounds with antibacterial activity. Examples of antibacterial compounds that are based on a tetramate nucleus are described in WO 2008/014311 and EP 1116715. In particular, EP 1116715 specifically describes reutericyclin both in racemic and (R) form.

It is among the objects of embodiments of the present invention to provide alternative compounds that can be used for the preparation and/or development of antibacterial compositions, and, in particular, antibacterial compositions for topical use.

SUMMARY OF THE INVENTION

In one aspect of the present invention, there is provided a compound as defined herein.

In another aspect, the present invention provides an antimicrobial composition comprising a compound as defined herein. Preferably, the composition is a topical composition.

In another aspect, the present invention provides the use of a compound as defined herein as an antimicrobial agent, such as a preservative.

In another aspect of the present invention, there is provided a compound as defined herein for use as a medicament for treating a topical microbial infection, such as a bacterial or fungal infection.

The present invention further provides a method of synthesising a compound as defined herein.

The present invention also provides a method of inhibiting bacterial RNA polymerase and/or undecaprenyl pyrophosphate synthase, which method comprising contacting a cell with an effective amount of a compound as defined herein.

In another aspect, the present invention provides a compound obtainable by, or obtained by, or directly obtained by a method of synthesis as defined herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

In this specification, the term "hydrocarbyl" refers to any substituent that consists of carbon and hydrogen atoms. The hydrocarbyl group may be saturated or unsaturated, or aromatic or aliphatic. The hydrocarbyl group may also be cyclic, straight chain or branched. Cyclic hydrocarbyl groups include monocyclic and polycyclic groups. Polycyclic groups include fused ring and bridged ring systems.

In this specification the term "alkyl" includes cyclic and non-cyclic, such as straight and branched chain alkyl groups.

The term "alkenyl" refers to hydrocarbyl groups containing at least one C=C bond. Alkenyl groups include cyclic, straight chain and branched alkenyl groups.

The term "aryl" refers to substituents comprising a cyclic, e.g. monocyclic or polycyclic aromatic ring having at least 5 carbon atoms. The aryl group is preferably an aryl hydrocarbyl group. Examples of aryl groups include, but are not limited to, phenyl, biphenyl, naphthyl and the like. In one embodiment, the aryl group may include a linking group attached the cyclic or polycyclic aromatic ring. The linking group may be of the formula $-[CR_{14}R_{15}]_t-$, where t is an integer of from 0 to 12, and $R_{14}$ and $R_{15}$ are each independently selected from H or $C_1$ to $C_2$ alkyl. For example, the aryl group may be $-C_6H_5$ or $-CH_2C_6H_5$. Thus, if a particular substituent, such as a hydrocarbyl group, is substituted with an aryl group, the substitution may take place via the linking group.

The term "halo" refers to fluoro, chloro, bromo and iodo.

The term "haloalkyl" is used herein to refer to an alkyl group in which one or more hydrogen atoms have been replaced by halogen atoms. The term "trihaloalkyl" refers to alkyl groups in which three hydrogen atoms have been replaced by halogen atoms, such as fluoroatoms. An example of a trihaloalkyl is trifluoroalkyl, $-CF_3$.

The term "heterocyclyl", "heterocyclic" or "heterocycle" covers aromatic, non-aromatic, saturated or unsaturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from at least one of nitrogen, oxygen or sulphur in the ring. Bicyclic heterocycles contain from about 7 to about 17 ring atoms, suitably from 7 to 12 ring atoms. Bicyclic heterocyclic(s) rings may be fused, spiro, or bridged ring systems. Where the heterocycle comprises two or more ring structures, a heteroatom may be present in one or more of the rings. In one embodiment, the heterocycle group may include a linking group attached thereto. The linking group may be of the formula —[$CR_{14}R_{15}$]$_t$—, where t is an integer of from 0 to 12, and $R_{14}$ and $R_{15}$ are each independently selected from H or $C_1$ to $C_2$ alkyl. Thus, if a particular substituent, such as a hydrocarbyl or heterocyclic group, is substituted with another heterocyclic group, the substitution may occur via the linking group.

As the skilled person would appreciate, any heterocycle may be linked to another group via any suitable atom, such as via a carbon or nitrogen atom.

By "bridged ring systems" is meant ring systems in which two rings share more than two atoms, see for example *Advanced Organic Chemistry*, by Jerry March, 4$^{th}$ Edition, Wiley Interscience, pages 131-133, 1992.

As discussed above, the heterocyclic group may be an aromatic heterocyclic group (hereinafter a "heteroaryl" group). Examples of such heteroaryls include aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings.

By "bridged ring systems" is meant ring systems in which two rings share more than two atoms, see for example *Advanced Organic Chemistry*, by Jerry March, 4$^{th}$ Edition, Wiley Interscience, pages 131-133, 1992.

As discussed above, the heterocyclic group may be an aromatic heterocyclic group (hereinafter a "heteroaryl" group). Examples of such heteroaryls include aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings.

The term "optionally substituted" refers to either groups, structures, or molecules that are substituted and those that are not substituted.

Where optional substituents are chosen from "one or more" groups it is to be understood that this definition includes at least one of the substituents being chosen from one of the specified groups or two or more of the substituents being chosen from two or more of the specified groups. It is not necessary for all substituents to be chosen from one of the specified groups, although this may be preferred.

The phrase "compound of the invention" means those compounds which are disclosed herein, both generically and specifically. For the avoidance of doubt, the term "compound" covers the compound per se, as well as salts (including pharmaceutically acceptable salts) and solvates thereof.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Tetramic Acid Derivatives

In a first aspect, the present invention provides a compound of the Formula I or II below:

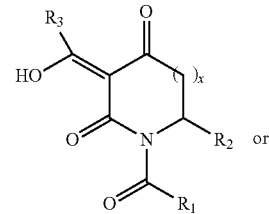

Formula I

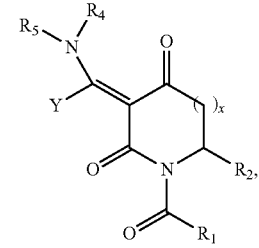

Formula II wherein
x is 0 or 1,
Y is OH or $C_1$ to $C_{15}$ alkyl,
$R_4$ is H or $C_1$ to $C_6$ alkyl,
either
$R_1$ is a $C_1$ to $C_{15}$ hydrocarbyl optionally substituted with a heterocyclic group or an ether group, and
$R_2$ is H, ether, thioether or $C_1$ to $C_8$ alkyl, or
$R_1$ and $R_2$ together form part of a 5-membered or 6-membered ring fused to the pyrrolidine/piperidine ring
$R_3$ and $R_5$ are each independently selected from a group of the formula $L_1$-$L_2$-$R_6$ or $L_2$-$L_1$-$R_6$, where $L_1$ is a linker of the formula —[$CR_8R_9$]$_n$—, where n is an integer of from 0 to 12, and $R_8$ and $R_9$ are in each instance each independently selected from H or $C_1$ to $C_2$ alkyl, and where $L_2$ is absent or a linker that is selected from O, S, SO, $SO_2$, N(R'), C(O), C(O)O, $[O(CH_2)_r]_s$, $[(CH_2)_rO]_s$, OC(O), CH(OR'), C(O)N(R'), N(R')C(O), N(R')C(O)N(R'), $SO_2N(R')$ or $N(R')SO_2$, where R' and R" are each independently selected from hydrogen and a $C_1$ to $C_2$ alkyl, and where r is 1 or 2 and s is 1 to 4, where $R_6$ is selected from $OR^{11}$, a heterocyclic and $C_1$ to $C_{25}$ hydrocarbyl group, wherein $R^{11}$ is a $C_1$ to $C_6$ alkyl, and wherein said heterocyclic and hydrocarbyl group is optionally substituted with at least one functional group selected from alkyl, alkenyl, aryl, halo, trihaloalkyl, alcohol, thio-alcohol, keto, $S(O)R^{11}$, ester, thioester, =O, =S, alkanoyl, ether, thioether, amide, thioamide, urea, thiourea, amine and heterocyclic group, with the proviso that the compound is not a compound of the formula III or IV below:

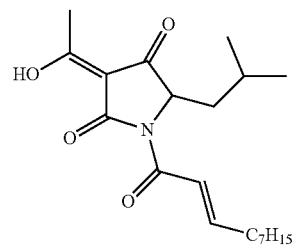

Formula III

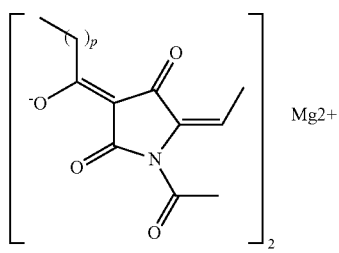

Formula IV wherein p is 2 or 4

When the compound is of Formula I and x=0, $R_3$ is preferably not methyl when $R_2$ is a $C_1$ to $C_5$ alkyl. When the compound is of Formula I and n=0, $R_3$ is preferably not methyl. When the compound is of Formula I and n=0, $R_2$ may or may not be a $C_1$ to $C_5$ alkyl. In one embodiment, $R_1$ is not $CH=CHC_7H_{15}$.

Where the compound is of Formula I and x=0, $R_3$ may be a $C_3$ to $C_7$ alkyl, such as a $C_3H_7$ or $C_5H_{11}$. In this embodiment, $R_2$ may be $CH_2CH(CH_3)_3$ and $R_1$ may be $CH=CHC_7H_{15}$.

The compounds of the present invention are useful in the development and/or manufacture of anti-microbial compositions, such as anti-bacterial or anti-fungal compositions. Without wishing to be bound by any theory, the antimicrobial activity is believed to be at least partially attributable to the tetramate nucleus and the substituent at the 3 position of the tetramate nucleus. The antimicrobial activity may also depend on the nature of the substituents at at least one of the $R_1$, $R_2$, $R_3$, $R_4$ and $R_5$ positions. By varying at least one of these substituents, the antimicrobial activity of the compound may be optimised. Accordingly, the present invention provides the means for developing and optimising lead compounds for the synthesis of antimicrobial (e.g. antibacterial or antifungal) actives. In another embodiment, the present invention provides compounds for use as antimicrobial actives, and, in particular, antibacterial actives for topical use.

In one embodiment, $R_4$ is H.

In another embodiment, $R_2$ is selected from hydrogen, a $C_1$ to $C_6$ alkyl or a thioether group of the formula $(CH_2)_qSR'$, where q is 1 to 4 and R' is a $C_1$ to $C_4$ alkyl group. Suitable alkyl groups include cyclic, straight chain or branched alkyl groups. Examples include methyl, ethyl, propyl (i-propyl or n-propyl) or butyl (n-butyl, t-butyl, s-butyl and i-butyl, preferably t-butyl). Branched alkyl groups, such as $CH_2CH(CH_3)_2$ are preferred. Where $R_2$ is a thioether group of the formula $(CH_2)_qSR'$, R' is preferably a methyl group. An example of a suitable thioether is $CH_2CH_2SCH_3$.

As noted above, $R_1$ may be a $C_1$ to $C_{15}$ hydrocarbyl group. This may be saturated or unsaturated, or aromatic or aliphatic. The hydrocarbyl group may be cyclic, straight chain or branched. In one embodiment, $R_1$ is an alkyl group. Suitable alkyl groups include straight chain alkyl groups, such as those of the formula $C_iH_{2i+1}$, where i is 1 to 10, preferably 3 to 6. Cyclic or branched alkyl groups may also be used. Such groups may also include hydrocarbyl linking groups, such as those of the formula $-[CR_{14}R_{15}]_t-$, where t is an integer of from 0 to 12, and $R_{14}$ and $R_{15}$ are each independently selected from H or $C_1$ to $C_2$ alkyl. Preferably, t is an integer from 0 to 6, for example, 1 to 3. In one embodiment, $R_1$ is an alkyl group selected from $C_3H_7$, $C_6H_{13}$ and $CH_2CH(CH_3)CH_2C(CH_3)_3$.

In another embodiment, the hydrocarbyl group may be or include an aryl group. Suitable aryl groups may have 6 to 12 carbon atoms. A preferred example is phenyl. These groups may also include hydrocarbyl linking groups, such as those of the formula $-[CR_{14}R_{15}]_t-$, where t is an integer of from 0 to 12, and $R_{14}$ and $R_{15}$ are each independently selected from H or $C_1$ to $C_2$ alkyl. Preferably, t is an integer from 0 to 6, for example, 1 to 3. The aryl group (e.g. phenyl) may optionally be substituted with a hydrocarbyl group, such as an alkyl group. Suitable alkyl groups include methyl groups. In one embodiment, $C_1$ is a phenyl group or a phenyl group substituted with a methyl group.

In another embodiment, the hydrocarbyl may be or include an alkenyl group. Such groups may include 2 to 10 carbon atoms. Such alkenyl groups may also include hydrocarbyl linking groups, such as those of the formula $-[CR_{14}R_{15}]_t-$, where t is an integer of from 0 to 12, and $R_{14}$ and $R_{15}$ are each independently selected from H or $C_1$ to $C_2$ alkyl. Preferably, t is an integer from 0 to 6, for example, 1 to 3. Where an alkenyl group is used, it may have a C=C bond at a position β to the C=O group. Preferably, the alkenyl group is of the formula $CH=CHC_iH_{2i+1}$, where i is an integer selected from 1 to 13. Specific examples of such groups include $CH=CHC_3H_7$ and $CH=CHC_7H_{15}$. The alkenyl group may be a cis- or trans-alkenyl and is preferably a trans-alkenyl group.

Where $R_1$ is or includes a hydrocarbyl group, the hydrocarbyl group may optionally be substituted with a heterocyclic group. An example of such a group is a thiophenyl group. For example, $R_1$ may be $CH_2C_4H_3S$. Where $R_1$ is or includes a hydrocarbyl group, the hydrocarbyl group may optionally be substituted with an ether group. Examples of suitable ether groups include those of the formula $OR_q$, where q is an alkyl, such as a $C_1$ to $C_6$ alkyl (e.g. methyl or ethyl) or an aryl group, such as a phenyl group. In one embodiment, $R_1$ is a phenyl group optionally substituted with an ether group, such as an $OCH_3$ group.

In another embodiment, $R_1$ and $R_2$ form a 5- or 6-membered ring structure, for example, as shown below:

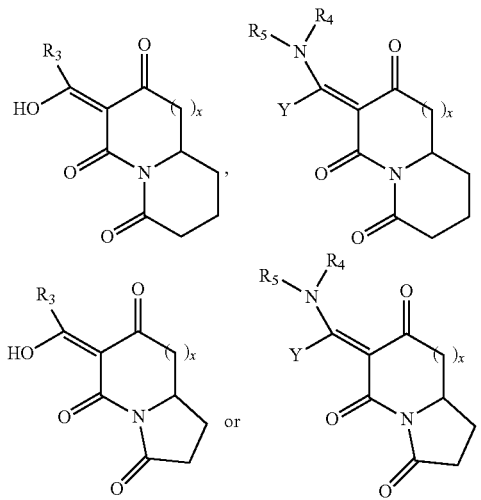

where x is 0 or 1, preferably 0. The 5- or 6-membered ring structure is preferably unsubstituted.

$R_3$ and $R_5$ are each a group of the formula $L_1$-$L_2$-$R_6$ or $L_2$-$L_1$-$R_6$, $L_1$-$L_2$-$R_6$ being preferred. As noted above, $L_1$ is a linker of the formula —$[CR_8R_9]_n$—, where n is an integer of from 0 to 12, and $R_8$ and $R_9$ are each independently selected from H or $C_1$ to $C_2$ alkyl. Preferably, n is from 0 to 11, more preferably 0 to 6, even more preferably 0 to 4, for example, 0 or 1. Preferably, $R_8$ and $R_9$ are each independently selected from H or methyl. Where more than one —$[CR_8R_9]$— link is present (i.e. n is greater than 1), $R_8$ may be the same or different in each instance of —$[CR_8R_9]$—. Similarly, $R_9$ may be the same or different in each instance of —$[CR_8R_9]$—.

As noted above, $L_2$ may be absent or a linker that is selected from O, S, SO, $SO_2$, N(R'), C(O), C(O)O, OC(O), $[O(CR'_2)_r]_s$, $[(CR'_2)_rO]_s$, CH(OR'), C(O)N(R'), N(R')C(O), N(R')C(O)N(R'), $SO_2$N(R') or N(R')$SO_2$ where R' and R" are each independently selected from hydrogen and a $C_1$ to $C_2$ alkyl, and where r is 1 or 2 and s is 1 to 4. In one embodiment, $L_2$ is absent. In another embodiment, $L_2$ is selected from O, C(O)O, OC(O), C(O)N(R') and N(R')C(O).

As mentioned above, $R_6$ is selected from $OR^{11}$, heterocyclic and $C_1$ to $C_{25}$ hydrocarbyl group. Where $R_6$ is $OR^{11}$, $R^{11}$ is a $C_1$ to $C_6$ alkyl, preferably a $C_1$ to $C_4$ alkyl group, such as methyl, ethyl, propyl (i-propyl or n-propyl) or butyl (n-butyl, t-butyl, s-butyl and i-butyl, preferably t-butyl).

$R_6$ may be a heterocyclic group. Suitable heterocyclic groups include aromatic and non-aromatic, saturated and unsaturated, and monocyclic and polycyclic heterocycles. Such groups may contain one or more heteroatoms, such as O, N and S. Where two or more heteroatoms are present, these may be the same or different. Where polycyclic heterocycles are used, the heteroatom may be present in one or more (e.g. all) of the cyclic groups. The heterocyclic group preferably has 5 to 12 ring members, for example, 5, 6, 7, 8 or 9 ring members. Suitable heterocyclic groups include saturated heterocyclic groups comprising 1 or 2 heteroatoms selected from O, N and S, preferably O and N. Examples of such saturated heterocycles include tetrahydrofuranyl, oxanyl, pyrrolidinyl, piperidinyl, azepanyl, morpholinyl, dioxanyl and piperazinyl. Suitable heterocyclic groups also include saturated heterocyclic groups comprising 1 or 2 heteroatoms selected from O, N and S. Examples of such unsaturated heterocycles include furanyl, pyrrol, imidazolyl, pyrazolyl, thiazolyl, isothiazolyl, diazinyl. The heterocycles may be fused to another ring, such as a cyclohexyl ring or benzene ring. Examples of such fused heterocycles include indole, isoindole and benzothiazole. The heterocyclic group may or may be coupled to the acyl group, nitrogen of the enamine group, $L_1$ or $L_2$ via the heteroatom. Alternatively, the attachment may be via a C atom. In one embodiment, the heterocycle comprises a ring N atom, which is optionally protected with a protecting group, such as t-BOC (t-butoxycarbonyl).

$R_6$ may be a $C_1$ to $C_{25}$ hydrocarbyl group. This may be saturated or unsaturated, or aromatic or aliphatic. The hydrocarbyl group may be cyclic, straight chain or branched. In one embodiment, $R_6$ is an alkyl group. Suitable alkyl groups include straight chain alkyl groups, such as those of the formula $C_iH_{2i+1}$, where i is 1 to 22, preferably 6 to 19. Cyclic alkyl groups, including monocyclic, polycyclic and bridged cycloalkyls, may also be used. Suitable monocyclic cycloalkyl groups may comprise $C_3$ to $C_6$ cycloalkyl groups, such as cyclopropane, cyclobutane, cyclopentyl and cyclohexyl. Such groups may also include hydrocarbyl linking groups, such as those of the formula —$[CR_{14}R_{15}]_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Suitable bridged cycloalkyls include adamantyl (e.g. 1-adamantyl), myrtanyl, norbornane and 6,6-dimethylbicyclo[3.1.1]heptan-2-yl)methyl. The bridged cycloalkyl substituent may be substituted, for example, with alkyl groups, such as methyl or ethyl groups, or alkanoyl group(s), such as acetyl. Such bridged cycloalkyl substituents may also include hydrocarbyl linking groups, such as those of the formula —$[CR_{14}R_{15}]_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3. In one embodiment, $R_6$ is or comprises a norbornane group that is optionally substituted, for example, with an acetyl group specific example is 2-norbornaneacetyl.

In another embodiment, the hydrocarbyl group may be or include an aryl group. Suitable aryl groups may have 6 to 12 carbon atoms. A preferred example is phenyl. These groups may also include hydrocarbyl linking groups, such as those of the formula —$[CR_{14}R_{15}]_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

In another embodiment, the hydrocarbyl may be or include an alkenyl group. Such groups may be derived from the alkyl groups defined above by replacing at least one C—C bond with a C=C bond. A specific example is 1-cyclohexene. Such alkenyl groups may also include hydrocarbyl linking groups, such as those of the formula —$[CR_{14}R_{15}]_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

As mentioned above, the heterocyclic group or hydrocarbyl group may be substituted with at least one functional group selected from alkenyl, alkyl, aryl, halo, trihaloalkyl, alcohol, keto, thioketo, sulfonyl, thio-alcohol, ester, thioester, ether, thioether, amide, thioamide, urea, thiourea, =O, =S, sulfonyl and heterocyclic groups. These substituents, particularly, the aryl and heterocyclic groups may themselves be substituted further, for example, with alkenyl, alkyl, aryl, halo, trihaloalkyl, alcohol, keto, thioketo, sulfonyl, thio-alcohol, ester, thioester, ether, thioether, amide, thioamide, urea, thiourea, =O, =S, sulfonyl and heterocyclic groups, such as those described herein. Where the heterocyclic group or hydrocarbyl group is substituted, at least one substituent must be selected from alkenyl, alkyl, aryl, halo, trihaloalkyl, alcohol, keto, $S(O)R^{13}$, sulfonyl, thio-alcohol, ester, thioester, ether, thioether, amide, thioamide, urea, thiourea, =O, =S, amine and heterocyclic groups. Where two or more substituents are present on the heterocyclic group or hydrocarbyl group, the second and subsequent substituent may also be selected from alkenyl, alkyl, aryl, halo, trihaloalkyl, alcohol, keto, $S(O)R^{13}$, sulfonyl, thio-alcohol, ester, thioester, ether, thioether, amide, thioamide, urea, thiourea, =O, =S, alkanoyl, amine and heterocyclic groups.

The heterocyclic group or hydrocarbyl group may be substituted with any alkenyl group. Suitable alkenyl groups are those having at least one C=C bond. The C=C may be coupled directly to the heterocyclic group or hydrocarbyl group or via a linking group of the formula $-[CR_{14}R_{15}]_t-$, where t is an integer of from 0 to 12, and $R_{14}$ and $R_{15}$ are each independently selected from H or $C_1$ to $C_2$ alkyl. Preferably, t is an integer from 0 to 6, for example, 1 to 3. The alkenyl group may have 2 to 20 carbon atoms, for example, 2 to 6 carbon atoms. The alkenyl group may be cyclic, straight chain or branched.

Where the substituent is an alkyl group, cyclic, straight chain and branched alkyl groups may be used. Suitable alkyl substituents may have 1 to 20 carbon atoms, for example, 1 to 6 carbon atoms. Preferred alkyl groups include methyl, ethyl, propyl (i-propyl or n-propyl) or butyl (n-butyl, t-butyl, s-butyl and i-butyl).

Where the substituent is an aryl group, the aryl group may be or include a hydrocarbyl aryl. Examples of aryl groups include, but are not limited to, phenyl, biphenyl, naphthyl and the like. Phenyl is preferred. In one embodiment, the aryl group may include a linking group attached the cyclic or polycyclic aromatic ring. The linking group may be of the formula $-[CR_{14}R_{15}]_t-$, where t is an integer of from 0 to 12, and $R_{14}$ and $R_{15}$ are each independently selected from H or $C_1$ to $C_2$ alkyl. Preferably, t is an integer from 0 to 6, for example, 1 to 3. For example, the aryl group may be $-C_6H_5$ or $-CH_2C_6H_5$. The aryl group may itself be substituted, for example, with alkyl, aryl, halo, trihaloalkyl, alcohol, keto, thioketo, sulfonyl, thio-alcohol, ester, thioester, ether, thioether, amide, thioamide, urea, thiourea, =O, =S, sulfonyl and heterocyclic groups as described herein. Examples of suitable substituents include alkyl groups, such as $CH_3$, $C_2H_5$ and t-butyl groups. Other examples include $OCH_3$, $OC_2H_5$ and OPh, phenyl, $-OH$, $(CH_2)_gOH$, where g is 1 to 3, $OCH_3$, $OC_2H_5$, OPh, $SCH_3$, $SC_2H_5$, SPh, $NH_2N(CH_3)_2$, F, Cl, Br, $CF_3$, $C(O)CH_3$ and $S(O)CH_3$. In one embodiment, $R_6$ is or comprises a heterocyclic group, such as a furanyl group that is optionally substituted with a phenyl group, which, in turn, is optionally substituted with a $CF_3$ group.

Where the substituent is halo, it may be a F, Cl, Br or I group. One or more halo substituents may be present. Where more than one halo substituent is present, the halo groups may be the same or different. In one embodiment, $R_6$ is a $C_iF_{2i+1}$ group, such as a $C_6F_{13}$ group.

Where the substituent is a trihaloalkyl, the trihaloalkyl may be a trihalo($C_1$-$C_6$)alkyl. The halo substituent may be F, Cl, Br or I. The three halo substituents may be the same or different. Preferably, the trihaloalkyl is trihalomethyl, more preferably trifluoromethyl.

Where the substituent is an alcohol or a thioalcohol, the OH or SH substituent may be coupled directly to the heterocyclic or hydrocarbyl group. Alternatively, the OH substituent may be coupled to the heterocyclic or hydrocarbyl group via, for example, $-[CR_{14}R_{15}]_t-$, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is an ester, the substituent may have the formula $C(O)OR_{16}$ or $OC(O)R_{16}$, where $R_{16}$ is a $C_1$ to $C_6$ alkyl (preferably methyl or ethyl), benzyl or phenyl group. Where the substituent is a thioester, the substituent may have the formula $C(O)SR_{16}$ or $SC(O)R_{16}$. The $C(O)OR_{16}$, $OC(O)R_{16}$ or $C(O)SR_{16}$ or $SC(O)R_{16}$ thioester may be coupled directly to the heterocyclic group or hydrocarbyl group or via a linking group, for example, of the formula $-[CR_{14}R_{15}]_t-$, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is an ether, the ether substituent may have or may include a group having the formula $OR_{17}$, where $R_{17}$ is $C_1$ to $C_6$ alkyl, phenyl or benzyl. Preferably, $R_{17}$ is a methyl, ethyl, propyl (i-propyl or n-propyl) or butyl (n-butyl, t-butyl, s-butyl and i-butyl). Preferred ether substituents include $OCH_3$, $OC_4H_9$, $OCH(CH_3)_2$ and OPh. The $OR_{17}$ group may be coupled directly to the heterocyclic group or hydrocarbyl group or via a linking group, for example, of the formula $-[CR_{14}R_{15}]_t-$, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is a thioether, the thioether substituent may or may include a group having the formula $SR_{17}$, where $R_{17}$ is $C_1$ to $C_6$ alkyl, phenyl or benzyl. A preferred thioether substituent is SMe. The $SR_{17}$ group may be coupled directly to the heterocyclic group or hydrocarbyl group or via a linking group e.g. of the formula $-[CR_{14}R_{15}]_t-$, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is amide, the amide may have or may include a group of the formula $N(R_{18})C(O)R_{19}$ or $C(O)NR_{18}R_{19}$. $R_{18}$ may be selected from H and $C_1$ to $C_{10}$ alkyl, while $R_{19}$ may be a $C_1$ to $C_{15}$ alkyl, trihaloalkyl (e.g. a trihalo($C_1$-$C_{15}$)alkyl) or $OR_{20}$, where $R_{20}$ is a $C_1$ to $C_6$ alkyl. In one embodiment, $R_{18}$ is H or $C_1$ to $C_6$ alkyl. Examples of suitable amide groups include $HNC(O)C_9H_{19}$, $HNC(O)OC(CH_3)_3$, $HNC(O)C_6F_{13}$, $C(O)N(C_6H_{13})(C_6H_{13})$, $HNC(O)Ph$, $N(CH_3)C(O)C_{11}H_{23}$, and HNC(O)1-adamantyl. The $N(R_{18})C(O)R_{19}$ or $C(O)NR_{18}R_{19}$ group may be coupled directly to the heterocyclic group or hydrocarbyl group or via a linking group e.g. of the formula $-[CR_{14}R_{15}]_t-$, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is thioamide, the thioamide may have or may include a group having the formula $N(R_{18})C(S)R_{19}$ or $C(S)NR_{18}R_{19}$. The $N(R_{18})C(S)R_{19}$ or $C(S)NR_{18}R_{19}$ group may be coupled directly to the heterocyclic group or hydrocarbyl group or via a linking group e.g. of the formula $-[CR_{14}R_{15}]_t-$, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is urea, it may have the formula $R_{30}C(O)R_{31}R_{32}$, where $R_{30}$, $R_{31}$ and $R_{32}$ are independently selected from H and $C_1$ to $C_6$ alkyl, for example, methyl or ethyl.

Where the substituent is thiourea, it may have the formula $R_{30}C(S)R_{31}R_{32}$, where $R_{30}$, $R_{31}$ and $R_{32}$ are independently selected from H and $C_1$ to $C_6$ alkyl, for example, methyl or ethyl.

Where the substituent is a keto group, it may have or may include a group of the formula $C(O)R_{20}$, where $R_{20}$ is a $C_1$ to $C_6$ alkyl, such as a methyl, ethyl, propyl (i-propyl or n-propyl) or butyl (n-butyl, t-butyl, s-butyl and i-butyl). An example of a suitable keto group is a $C(O)CH_3$ group. In one embodiment, the keto group comprises an oxo substituted cycloalkyl group. The cycloalkyl group may have 4 to 8 carbon atoms, for example, 5 or 6 carbon atoms. The $C(O)R_{20}$ group may be coupled directly to the hydrocarbyl group or heterocyclic group or may be coupled via a linker, for example, of the formula —$[CR_{14}R_{15}]_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is of the formula $S(O)R_{13}$, $R_{13}$ may be $C_1$ to $C_6$ alkyl, preferably methyl. The $S(O)R_{13}$ may be coupled directly to the hydrocarbyl group or heterocyclic group or may be coupled via a linker, for example, of the formula —$[CR_{14}R_{15}]_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is a sulfonyl, it may include a substituent having the formula $SO_2R_{21}$, where $R_{21}$ is a $C_1$ to $C_6$ alkyl or a trihalo($C_1$ to $C_6$) alkyl, such as trifluoroalkyl. These groups may be coupled directly to the hydrocarbyl or heterocyclic group or via a linker, such as one of the formula —$[CR_{14}R_{15}]_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is an =O or =S group, these are typically coupled to a ring atom of, for example, a heterocyclic, aryl or cyclic hydrocarbyl (e.g. alkyl or alkenyl) group. In one embodiment, an =O substituent is provided on a cyclopentyl ring.

Where the substituent is an amine, the amine may be or comprise a group of the formula $NR_{22}R_{23}$, where $R_{22}$ and $R_{23}$ are independently selected from H and $C_1$ to $C_6$ alkyl. In one embodiment, both $R_{22}$ and $R_{23}$ are H. In another embodiment, $R_{22}$ and $R_{23}$ are independently selected from H, methyl and ethyl. Examples of preferred amine substituents are $NH_2$, $N(CH_3)_2$ and $N(C_2H_5)_2$. The amines may optionally be provided in salt form, for example, as a salt of HCl. The $NR_{22}R_{23}$ group may be coupled directly to the heterocyclic or hydrocarbyl group or may be coupled via a linking group, such as one of the formula —$[CR_{14}R_{15}]_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3. In one embodiment, $R_6$ is a hydrocarbyl group that is substituted with an amine group, where the amine group is protected with a protecting group, such as t-BOC (t-butoxycarbonyl).

Where the substituent is a heterocyclic group, it may be or may include aromatic and non-aromatic, saturated and unsaturated, and monocyclic and polycyclic heterocycles. Such groups may contain one or more heteroatoms, such as O, N and S. Where two or more heteroatoms are present, these may be the same or different. Where polycyclic heterocycles are used, the heteroatom may be present in one or more (e.g. all) of the cyclic groups. The heterocyclic group preferably has 5 to 12 ring members, for example, 5, 6, 7, 8 or 9 ring members. Suitable heterocyclic groups include saturated heterocyclic groups comprising 1 or 2 heteroatoms selected from O, N and S, preferably O and N. Examples of such saturated heterocycles include tetrahydrofuranyl, oxanyl, pyrrolidinyl, piperidinyl, azepanyl, morpholinyl, dioxanyl and piperazinyl. Suitable heterocyclic groups also include saturated heterocyclic groups comprising 1 or 2 heteroatoms selected from O, N and S. Examples of such unsaturated heterocycles include furanyl, pyrrol, imidazolyl, pyrazolyl, thiazolyl, isothiazolyl, diazinyl. The heterocycles may be fused to another ring, such as a cyclohexyl ring or benzene ring. Examples of such fused heterocycles include indole, isoindole and benzothiazole. The heterocyclic group may be coupled directly to the hydrocarbyl or heterocyclic group coupled to the enamine nitrogen. Alternatively, the heterocyclic group may be coupled indirectly via a linking group, such as one of the formula —$[CR_{14}R_{15}]_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3. In one embodiment, the heterocycle comprises a ring N atom, which is optionally protected with a protecting group, such as t-BOC (t-butoxycarbonyl).

The heterocyclic group may itself be substituted. Suitable substituents are alkyl, aryl, alcohol, ether, thioether, amine, halo, trihaloalkyl, trihaloalkylether, keto, $S(O)R_{25}$, where $R_{25}$ is a $C_1$ to $C_6$ alkyl. These substituents are as defined above. However, specific examples of such substituents include methyl, ethyl, phenyl, —OH, $(CH_2)_gOH$, where g is 1 to 3, $OCH_3$, $OC_2H_5$, OPh, $SCH_3$, $SC_2H_5$, SPh, $NH_2N(CH_3)_2$, F, Cl, Br, $CF_3$, $C(O)CH_3$ and $S(O)CH_3$.

In a preferred embodiment, $R_6$ is a phenyl group that is optionally substituted with at least one functional group selected from alkyl, aryl, halo, trihaloalkyl, alcohol, thioalcohol, ester, thioester, ether, thioether, amide, thioamide, urea, thiourea and heterocyclic group.

The phenyl group may be substituted with a group selected from cyclohexyl, $C_1$ to $C_3$ alkyl, halo, halo($C_1$ to $C_3$) alkyl, OH, SH, heterocyclic and $OR_{10}$ or $SR_{10}$, where $R_{10}$ is a $C_1$ to $C_4$ alkyl or phenyl group. Preferably, however, the phenyl group is substituted with a heterocyclic group selected from a piperidine and morpholine group, or where the phenyl group is fused to an aromatic heterocyclic ring, preferably a pyrrole ring.

In one embodiment, $R_6$ is selected from $CH_2CH(CH_3)$ $CH_2C(CH_3)_3$, cyclohexyl, adamantyl and phenyl optionally substituted with at least one functional group selected from acetyl, =O, $C_2$ to $C_6$ alkenyl, $C_1$ to $C_4$ alkyl and thioether.

In another embodiment, $R_6$ is selected from:

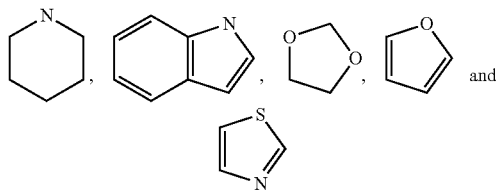

optionally substituted with at least one functional group selected from $OR^{12}$, =O and $C_1$ to $C_6$ alkyl, where $R_{12}$ is a $C_1$ to $C_4$ alkyl.

Examples of suitable compounds include:
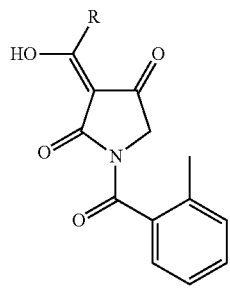
R = C₁₀H₂₁
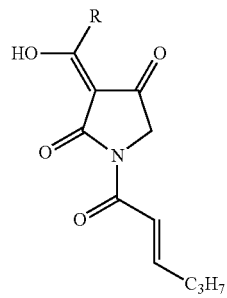
R = C₉H₁₉;
R = C₁₁H₂₃
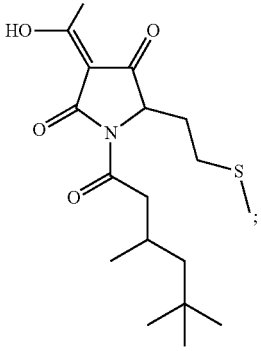
R = C₅H₁₁;
R = C₇H₁₅;
R = C₉H₁₉
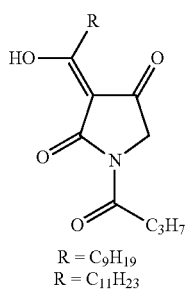
R = C₉H₁₉
R = C₁₁H₂₃
R = C₁₃H₂₇
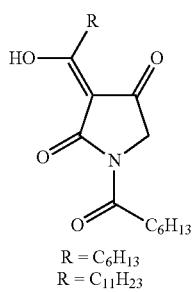
R = C₆H₁₃
R = C₁₁H₂₃
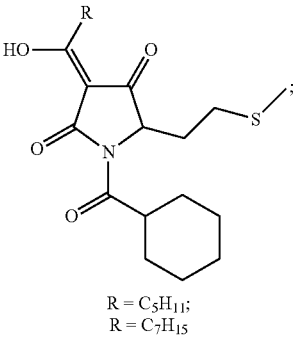
R = C₅H₁₁;
R = C₇H₁₅
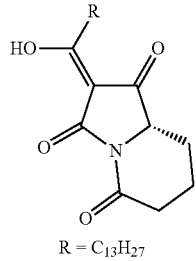
R = C₁₃H₂₇
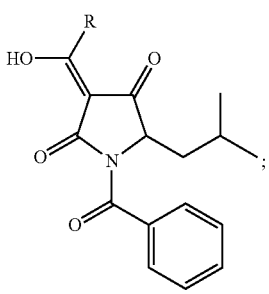
R = C₇H₁₅
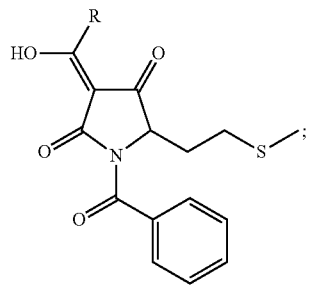
R = C₈H₁₇;
R = C₁₀H₂₁
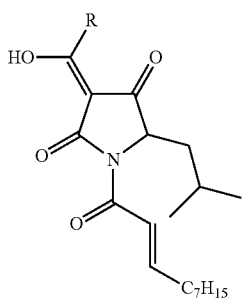
R = C₃H₇;
R = C₅H₁₁
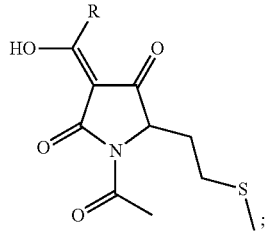
R = C₁₀H₂₁;
R = C₁₁H₂₃;
R = C₁₂₉H₂₅
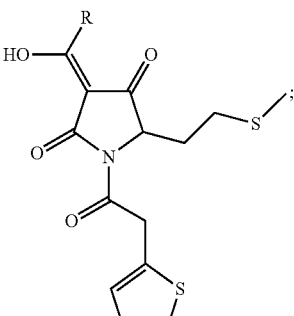
R = C₇H₁₅;
R = C₉H₁₉

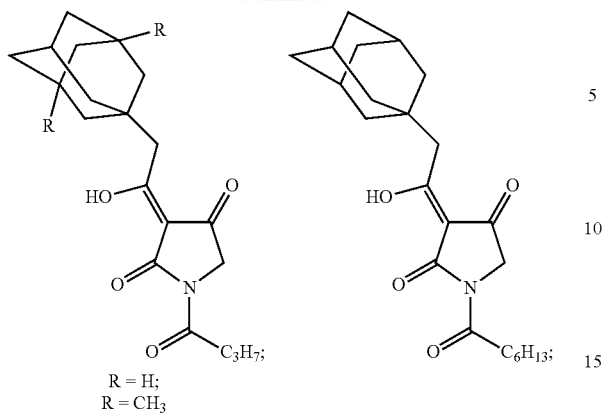
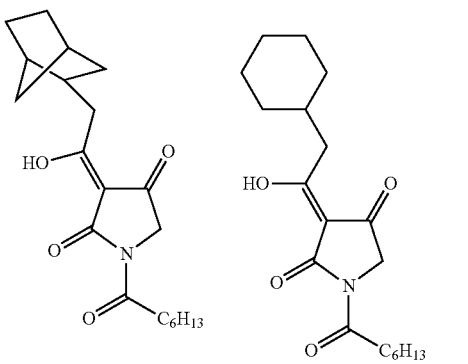
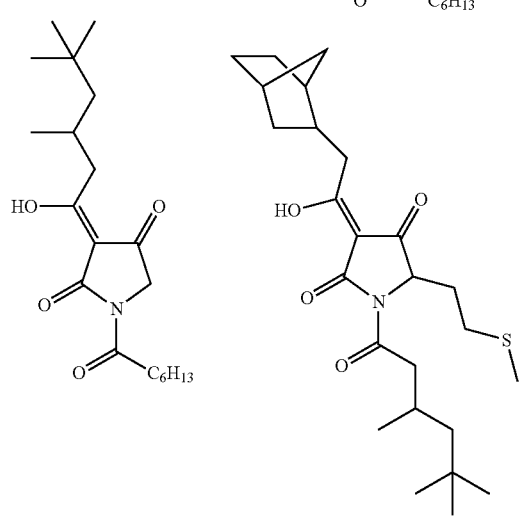
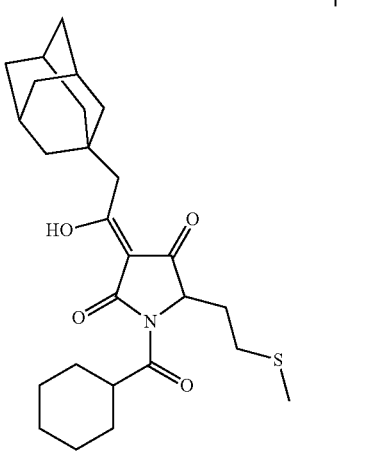
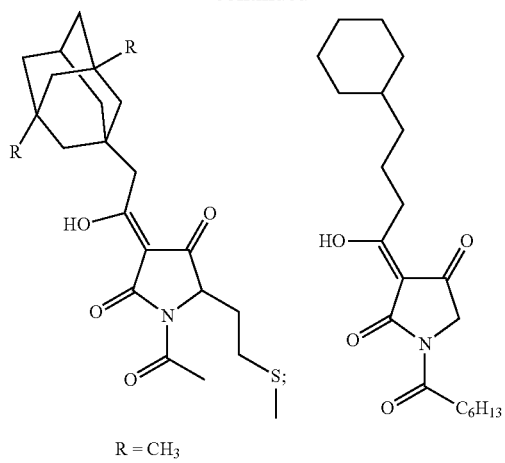
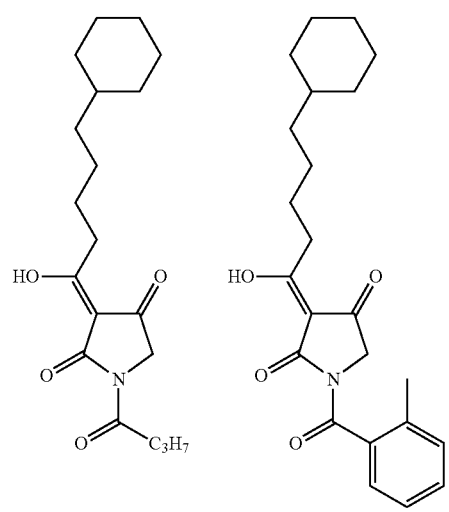
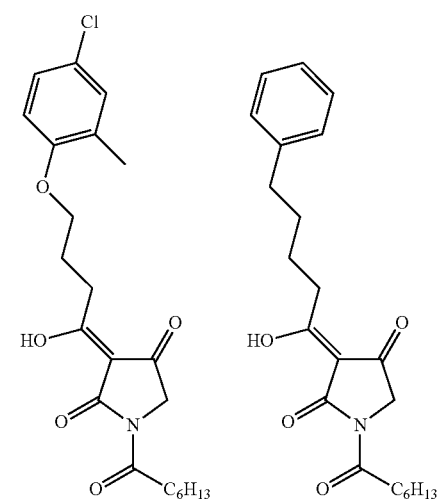

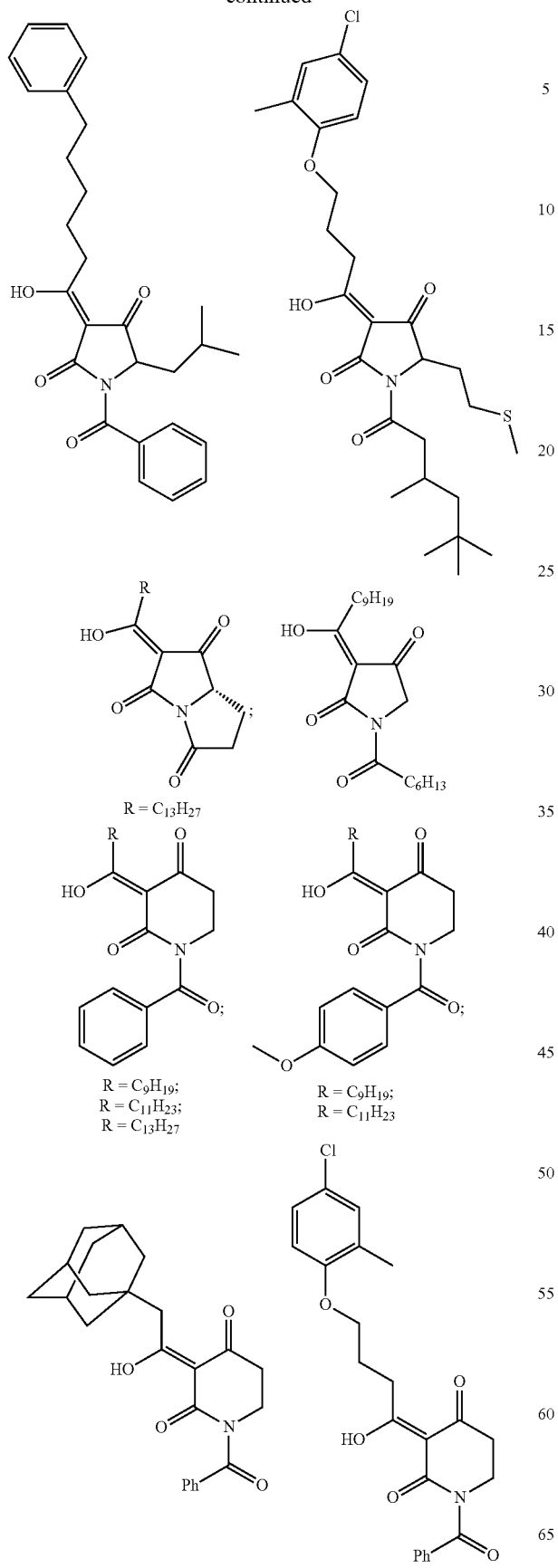
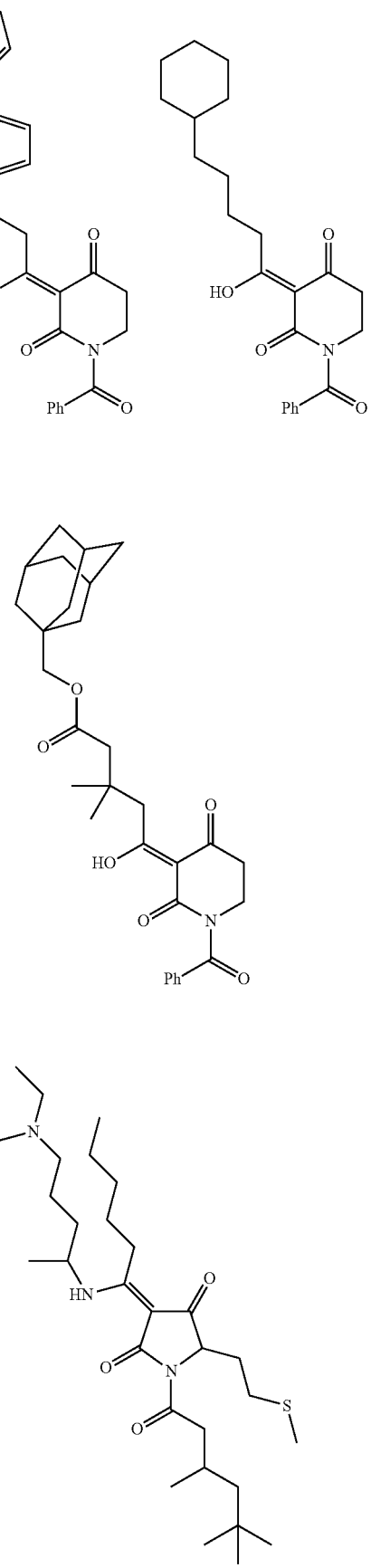

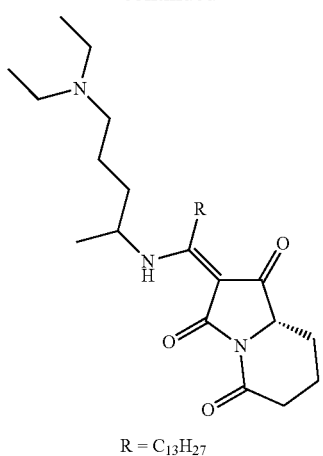
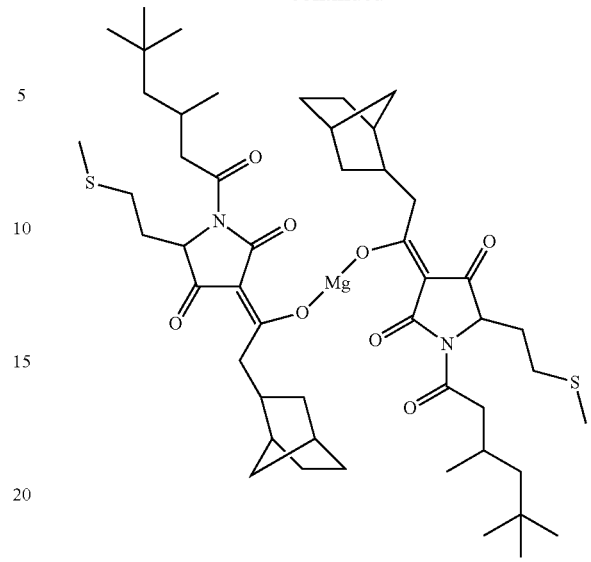
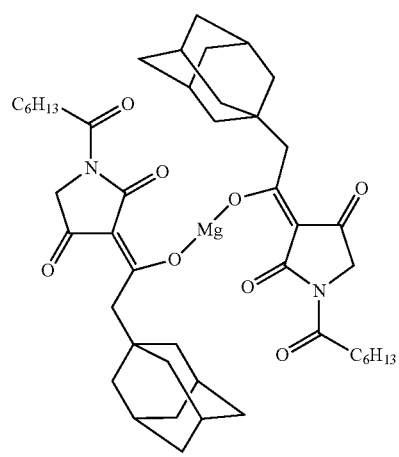
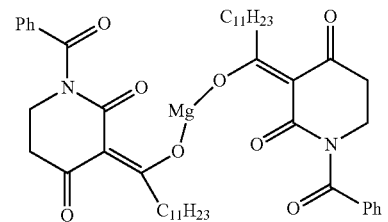
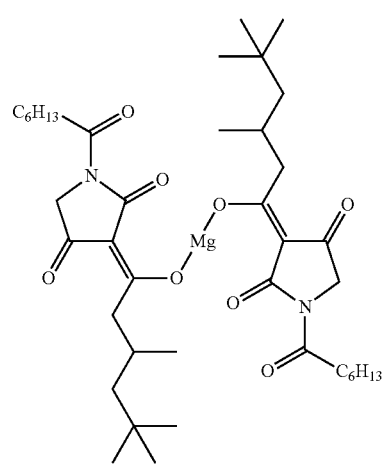
Preferred compounds are:
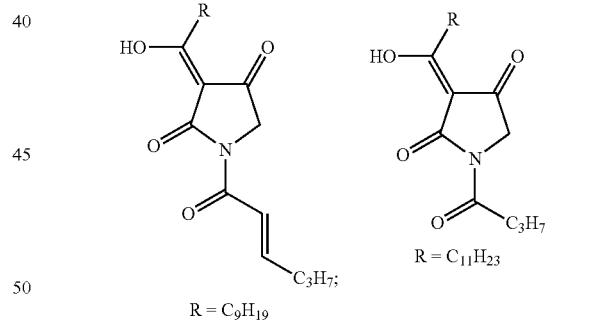
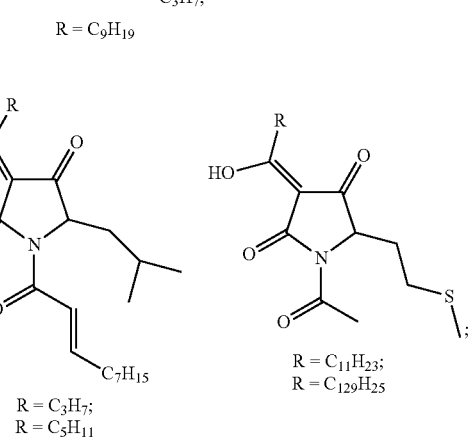

21
-continued
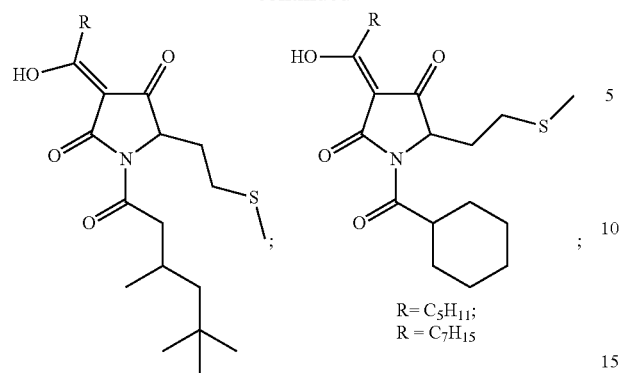
R = C5H11;
R = C7H15;
R = C9H19
R= C5H11;
R = C7H15
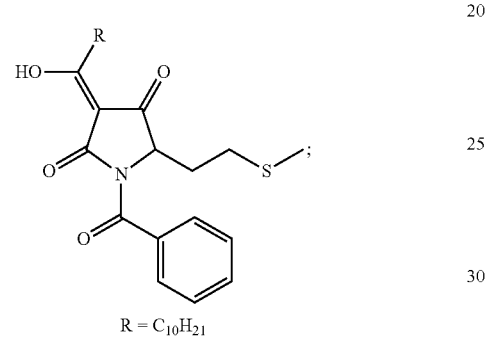
R = C10H21
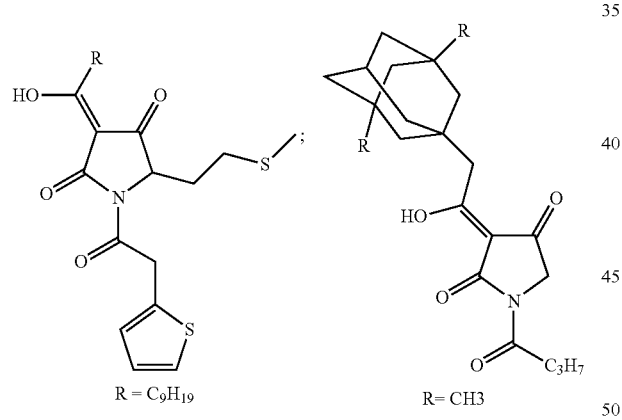
R = C9H19
R= CH3
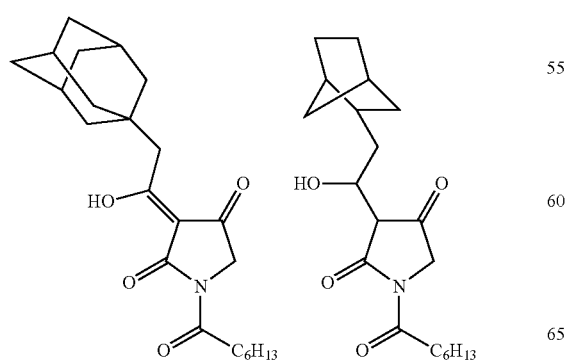
22
-continued
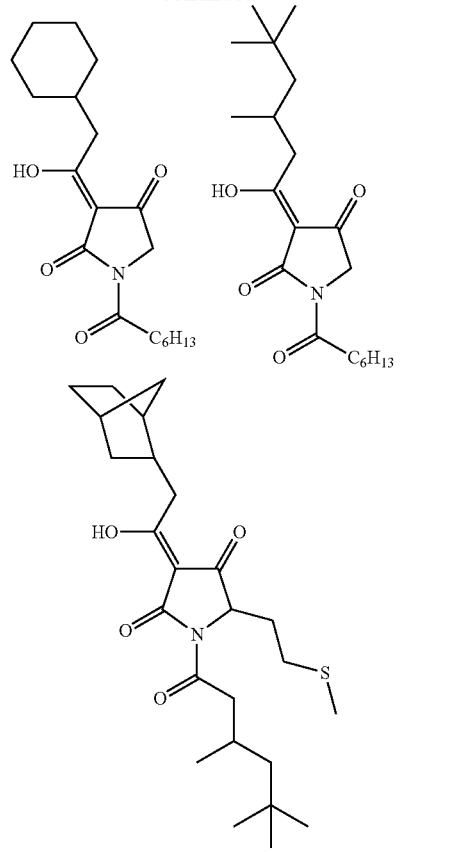
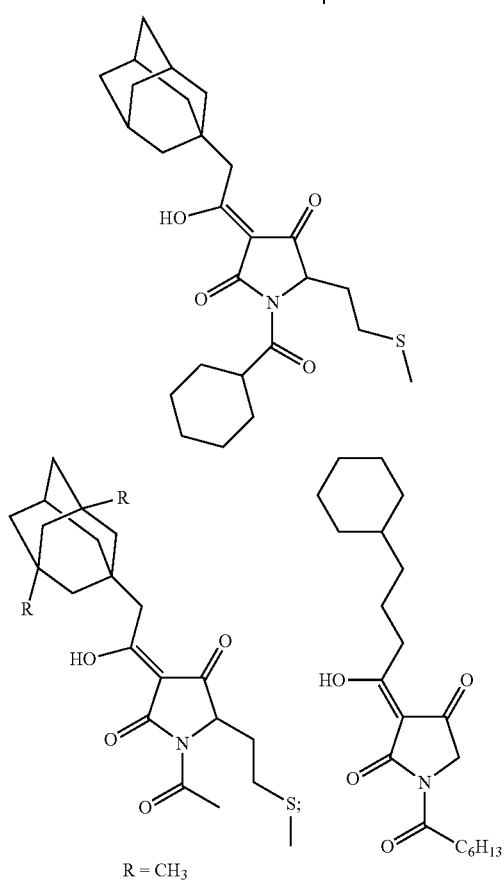
R = CH3

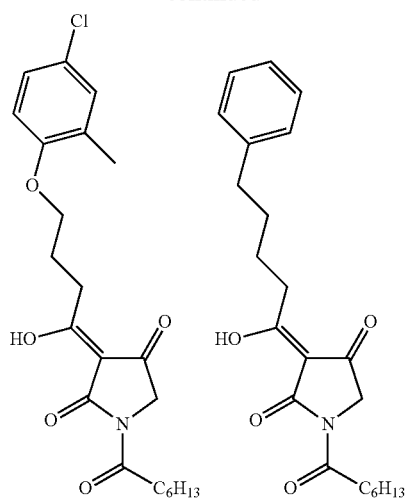
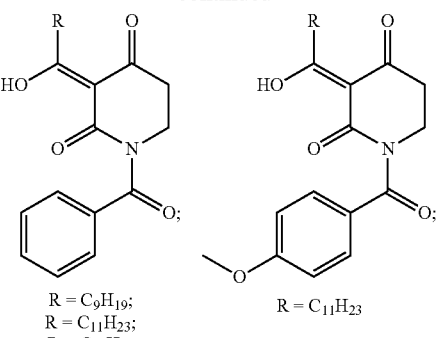
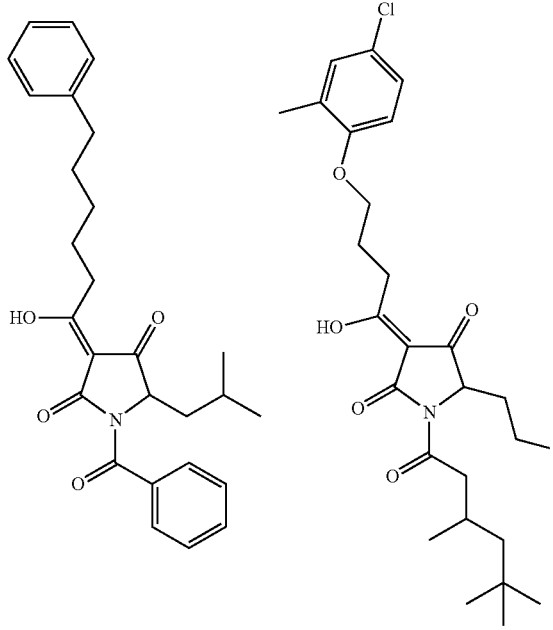
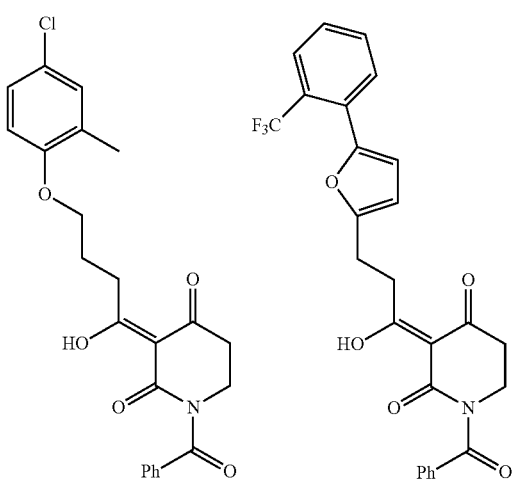
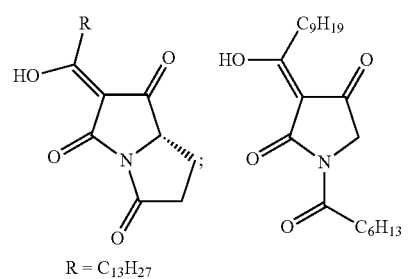

-continued
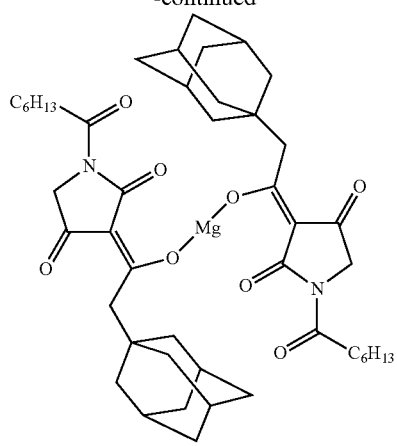
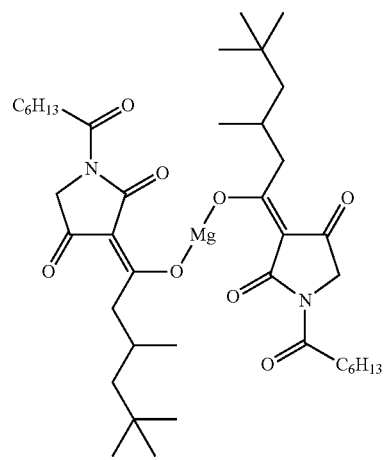
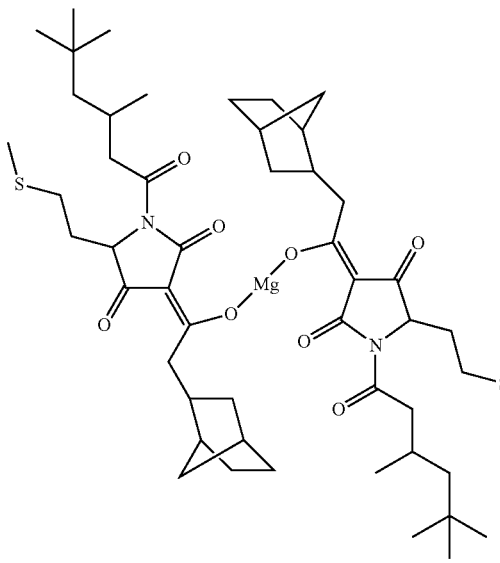
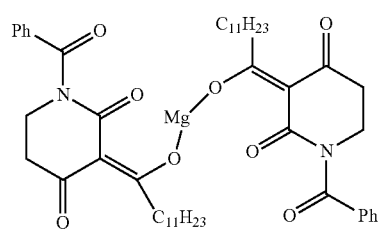
Yet more preferred compounds are:
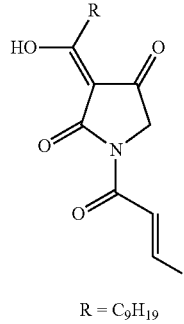
R = C₉H₁₉
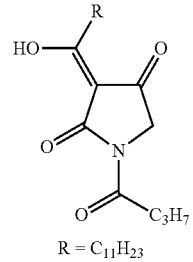
R = C₁₁H₂₃
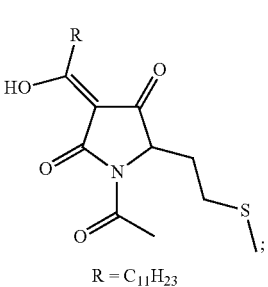
R = C₁₁H₂₃
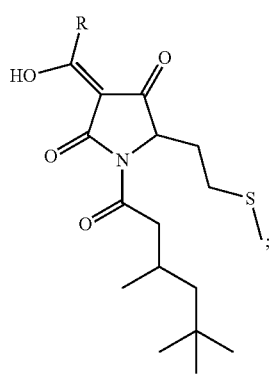
R = C₅H₁₁;
R = C₇H₁₅;
R = C₉H₁₉
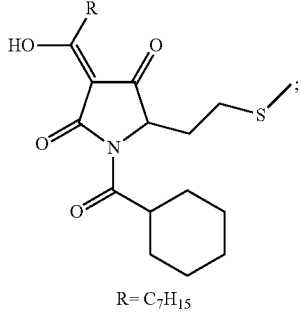
R = C₇H₁₅
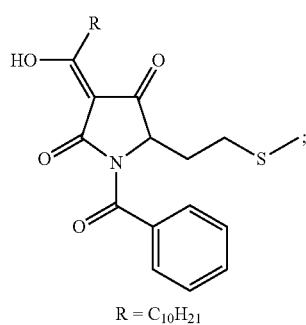
R = C₁₀H₂₁

27
-continued
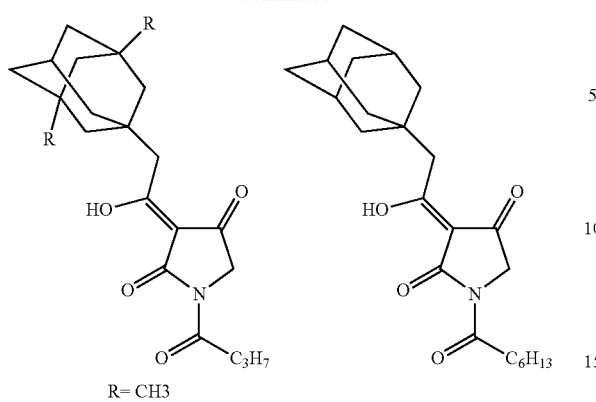
28
-continued
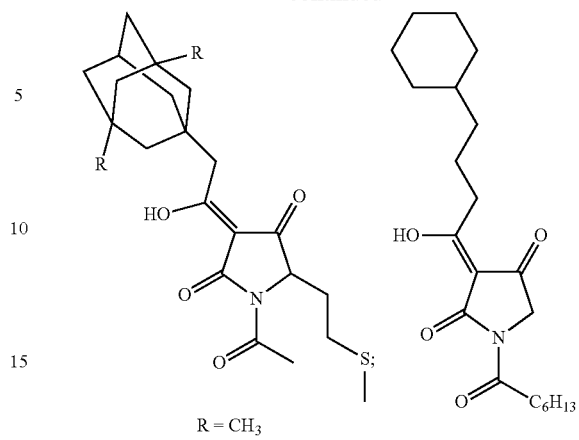
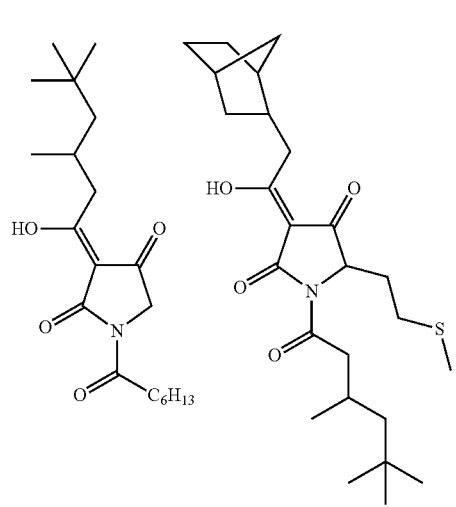
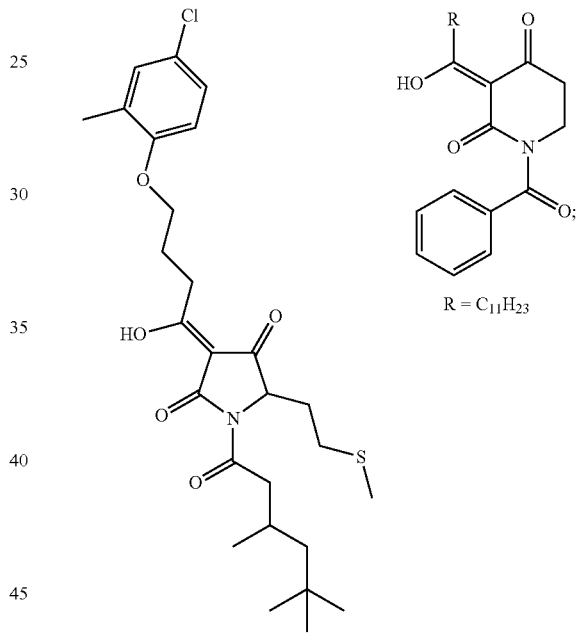
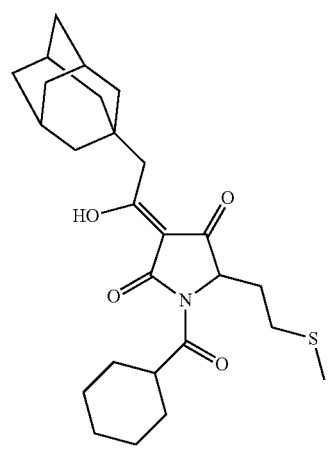
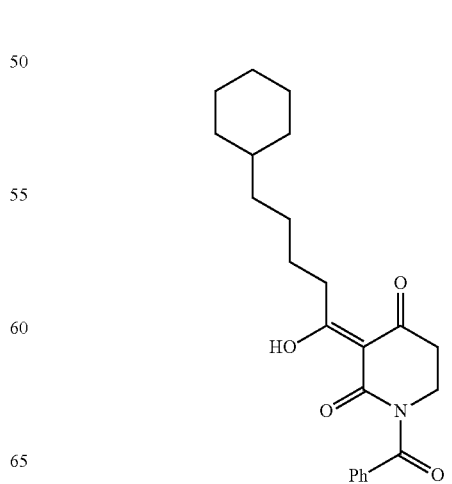

-continued

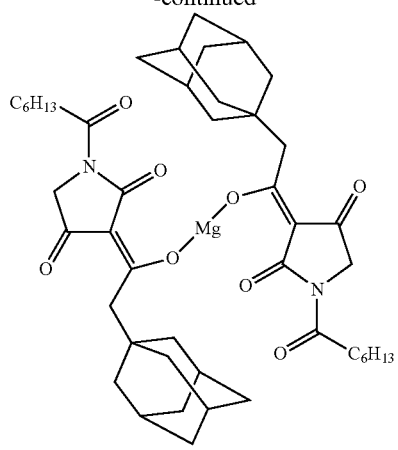

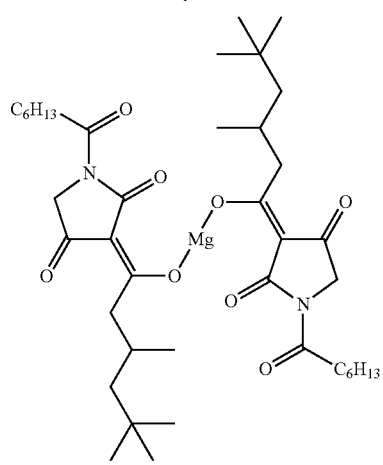

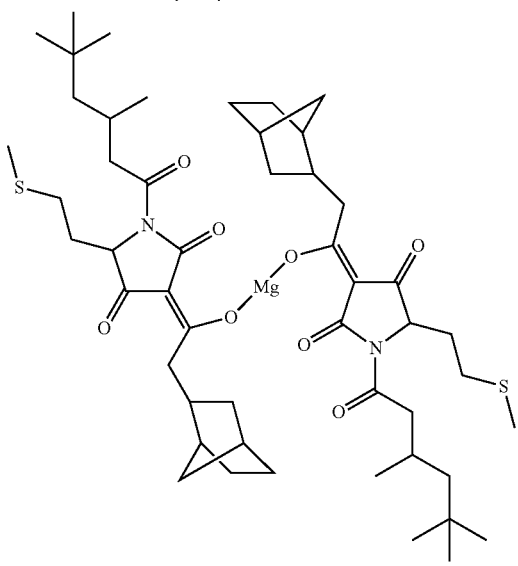

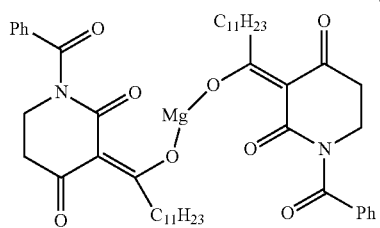

The following compounds are especially preferred:

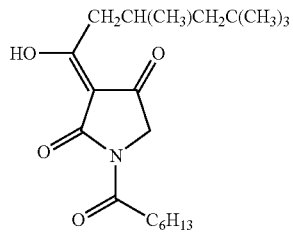

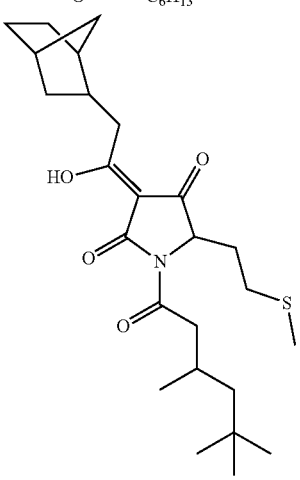

Suitable or preferred features of any compounds of the present invention may also be suitable features of any other aspect.

A suitable pharmaceutically acceptable salt of a compound of the invention is, for example, a magnesium salt.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof.

It is also to be understood that certain compounds of the invention may exist in solvated as well as unsolvated forms such as, for example, hydrated forms. It is to be understood that the invention encompasses all such solvated forms.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below).

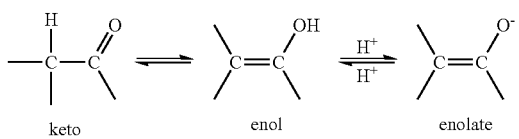

It shall also be appreciated that compounds of the present invention may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

The compounds of the present invention are useful as antimicrobial (e.g. antibacterial or antifungal agents). Accordingly, a further aspect of the present invention provides an antimicrobial composition, preferably a topical antibacterial or antifungal composition, comprising a compound as defined herein. As discussed above, the reference to "compound" covers all isomers of that compound as well as salts and solvates thereof.

The compounds of the present invention may be used as an antimicrobial compound in paper, fabric, building materials, packaging materials, coating and paint compositions, disinfectants, detergents, household products, cosmetics and suncreams.

The compounds of the present invention may be capable of inhibiting bacterial RNA polymerase and/or undecaprenyl pyrophosphate synthase. Accordingly, a further aspect of the invention provides a method of inhibiting bacterial RNA polymerase and/or undecaprenyl pyrophosphate synthase, which comprises contacting a cell with an effective amount of a compound as defined herein (or a pharmaceutically acceptable salt thereof). This contacting step may be performed ex-vivo or on the surface of a human or animal's skin.

The compounds of the present invention may be effective against Gram positive and/or Gram negative bacteria. For example, the compounds may be effective against Gram positive bacteria selected from at least one of Metchillin-resistant *S. Aureus*; Penicillin and erythromycin-resistant *S. pneumonia*; Vancomycin resistant *E. Faecium*; and Vancomycin susceptible *E. Faecalis*. Alternatively or additionally the compounds may be effective against Gram negative bacteria, such as *H. influenzae*. Some embodiments of the present invention are active against Gram positive bacteria but only weakly active against Gram negative bacteria. Preferred embodiments of the present invention are especially active against bacteria, such as MRSA (Methicillin resistant *Staphylococcus aureus*), MDR (multi-drug resistant bacteria), PRSP (Penicillin resistant *Streptococcus pneumoniae*) and VRE (Vancomycin resistant *enterococcus*).

In a preferred embodiment, the compounds of the present invention exhibit a minimum inhibitory concentration (MIC) of 16 μg/ml or less, preferably 12 μg/ml or less, more preferably 10 μg/ml or less, even more preferably 8 μg/ml or less, yet more preferably 6 μg/ml or less. In one embodiment, the MIC is 4 μg/ml or less, preferably less than 4 μg/ml or less, for example, 2 μg/ml or less. The compounds may exhibit the above MIC's against at least one bacteria selected from Gram positive and Gram negative bacteria. Examples of bacteria are discussed herein. Specific examples are discussed herein.

Procedures for determining MIC are well known in the art. For example, for bacteria, MICs may be determined based the Clinical and Laboratory Standards Institute (CLSI) methodology (Methods for dilution antimicrobial susceptibility tests for bacteria that grow aerobically; Approved Standard—seventh edition. 2006, M7-A7, CLSI, Wayne Pa.) by a 2-fold broth dilution technique in Mueller Hinton (pH7.4 Biorad). Overnight cultures may be diluted to obtain the final inoculum of 105 cfu/well. Incubation was 37° C. overnight in ambient air. The MIC may be defined as the lowest concentration which inhibited all visual growth and expressed in μg/ml. For each bacterial species, all of the molecules were tested in the same experiment in order to give a head-to-head comparison.

For fungi, MICs may be determined for the antifungus by microdilution methods using RPMI 1640 medium buffered with morpholinopropanesulfonic acid (MOPS) and supplemented with L-glutamine as described by CLSI procedures (M27-A method) (Reference method for broth dilution antifungal susceptibility testing of yeasts; Approved standard—third edition. 2006, M27-A2, CLSI, Wayne Pa.). After incubation for 24-48 hours at 35° C., the lowest concentration of drug which produced 80% reduction in visible growth compared with control may be considered as the MIC.

Synthesis

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

In one aspect, there is provided a method of synthesising a compound of the Formula I, which comprises:
reacting a compound of the formula V below

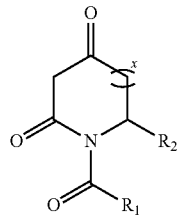

V with a carboxylic acid of the formula $R_3CO_2H$; or
reacting a compound of the formula V with i) a carboxylic acid of the formula $R_3CO_2H$ or ii) an acid chloride of the formula $R_3COCl$ to form a compound of the formula VI below,

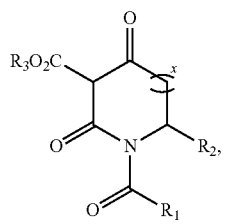

VI and
reacting the compound of the Formula VI with a base (preferably 4-dimethylaminopyridine or triethylamine) to convert the O-acyl derivative to the corresponding C-acyl derivative.

In another aspect, the present invention also provides a method of synthesising a compound of the Formula II, wherein Y is not OH, which comprises reacting a compound of Formula I with an amine of the formula $R_4R_5NH$.

In yet another aspect, the present invention provides a method of synthesising a compound of the Formula II, which comprises reacting a compound of the formula V with a compound of the formula $R_5$—NCO, or
reacting a compound of the formula VI', where R is a hydrocarbyl group or $R_3$, or preferably a $C_1$ to $C_6$ alkyl group,

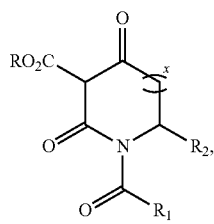

VI' with an amine of the formula $R_4R_5NH$, with the proviso that, where compound V is reacted with $R_5NCO$, $R_4$ is H.

The compound of Formula VI' may be formed by acylating a compound of Formula V, preferably with $R_3OC(O)Cl$.

The compound of the formula V may be prepared by reacting a compound of the Formula VII or VIII below with meldrum's acid in the presence of N,N'-Dicyclohexylcarbodiimide (DCC) and 4-dimethylaminopyridine (DMAP). Thereafter, the product is reacted with ethyl acetate under reflux.

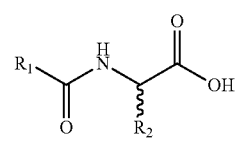

Formula VII

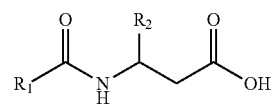

Formula VIII

A preferred synthetic route is shown in the scheme below:

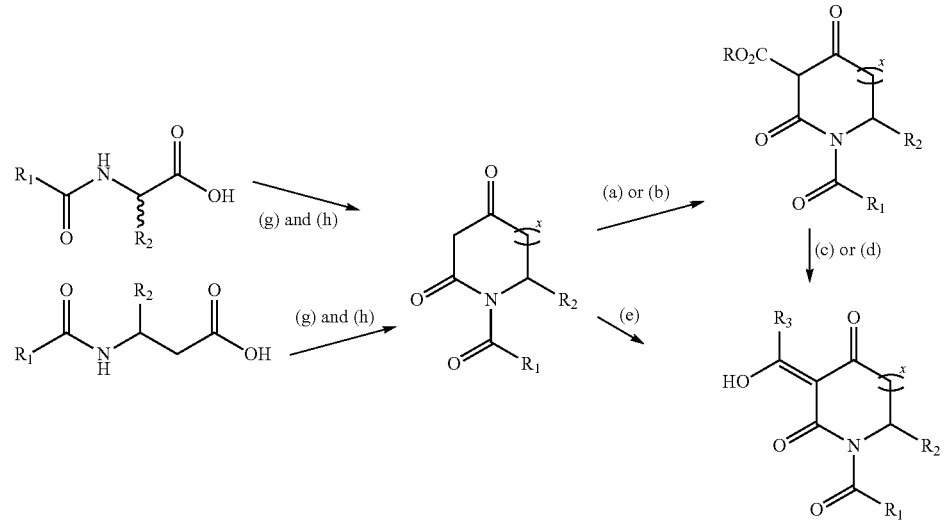

Reaction conditions; (a) $R_3CO_2H$ (1.1 eq), DCC (1.1 eq), DMAP (0.1 eq), $CH_2Cl_2$, r.t.; (b) $R_3COCl$ (1.1 eq), triethylamine (1.2 eq), $CH_2Cl_2$, r.t.; (c) $(CH_3)_2C(OH)CN$ (0.5 eq), triethylamine (2.0 eq), $CH_3CN$, r.t.; (d) DMAP (1.3 eq), $CH_2Cl_2$, r.t.; (e) $R_3CO_2H$ (1.1 eq), DCC (1.1 eq), DMAP (1.3 eq), $CH_2Cl_2$, r.t.; (f) trifluoroacetic acid, $CH_2Cl_2$, r.t.; (g) meldrum's acid (1.1 eq), DCC (1.1 eq), DMAP (1.1 eq), $CH_2Cl_2$, r.t. (h) ethyl acetate, reflux;

EXAMPLES

The following compounds were tested in the Examples:

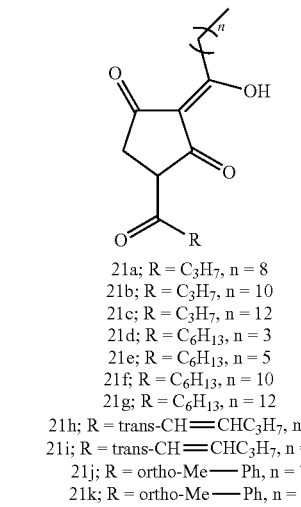

21a; R = C$_3$H$_7$, n = 8
21b; R = C$_3$H$_7$, n = 10
21c; R = C$_3$H$_7$, n = 12
21d; R = C$_6$H$_{13}$, n = 3
21e; R = C$_6$H$_{13}$, n = 5
21f; R = C$_6$H$_{13}$, n = 10
21g; R = C$_6$H$_{13}$, n = 12
21h; R = trans-CH=CHC$_3$H$_7$, n = 8
21i; R = trans-CH=CHC$_3$H$_7$, n = 10
21j; R = ortho-Me—Ph, n = 7
21k; R = ortho-Me—Ph, n = 9

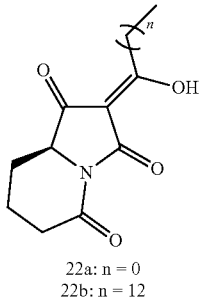

22a: n = 0
22b: n = 12

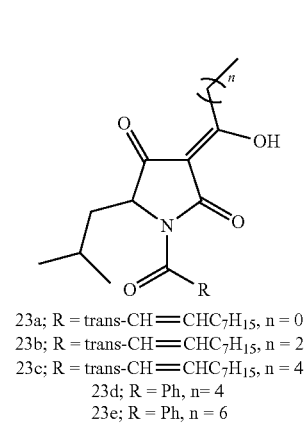

23a; R = trans-CH=CHC$_7$H$_{15}$, n = 0
23b; R = trans-CH=CHC$_7$H$_{15}$, n = 2
23c; R = trans-CH=CHC$_7$H$_{15}$, n = 4
23d; R = Ph, n = 4
23e; R = Ph, n = 6

24a; R = Me, n = 9
24b; R = Me, n = 10
24c; R = Me, n = 11
24d; R = cyclohexyl, n = 4
24e; R = cyclohexyl, n = 6
24f; R = Ph, n = 7
24g; R = Ph, n = 9

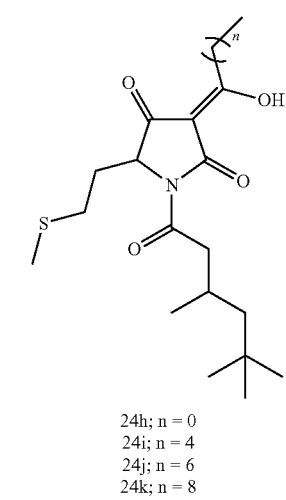

24h; n = 0
24i; n = 4
24j; n = 6
24k; n = 8

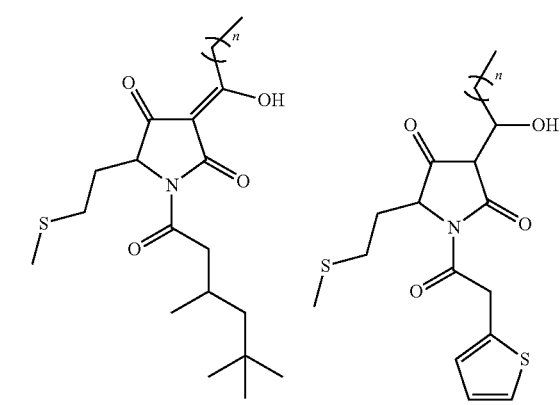

24l; n = 6
24m; n = 8

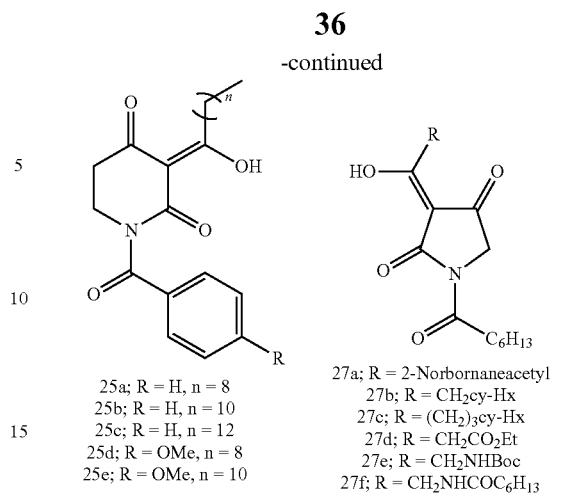

25a; R = H, n = 8
25b; R = H, n = 10
25c; R = H, n = 12
25d; R = OMe, n = 8
25e; R = OMe, n = 10

27a; R = 2-Norbornaneacetyl
27b; R = CH$_2$cy-Hx
27c; R = (CH$_2$)$_3$cy-Hx
27d; R = CH$_2$CO$_2$Et
27e; R = CH$_2$NHBoc
27f; R = CH$_2$NHCOC$_6$H$_{13}$
27g; R = CH$_2$(OC$_2$H$_4$)$_2$OCH$_3$
27h; R = CH$_2$CH(CH$_3$)CH$_2$C(CH$_3$)$_3$

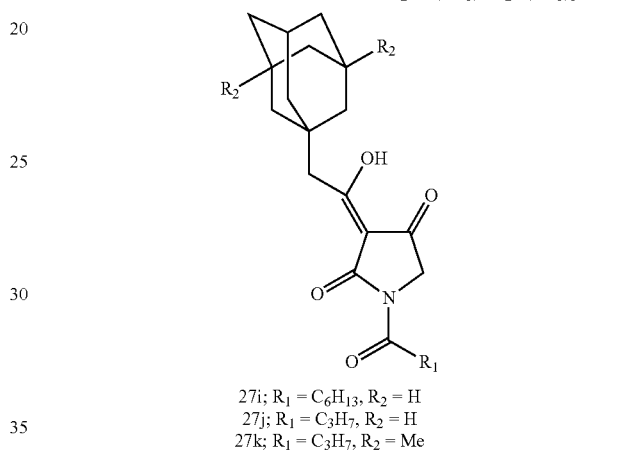

27i; R$_1$ = C$_6$H$_{13}$, R$_2$ = H
27j; R$_1$ = C$_3$H$_7$, R$_2$ = H
27k; R$_1$ = C$_3$H$_7$, R$_2$ = Me

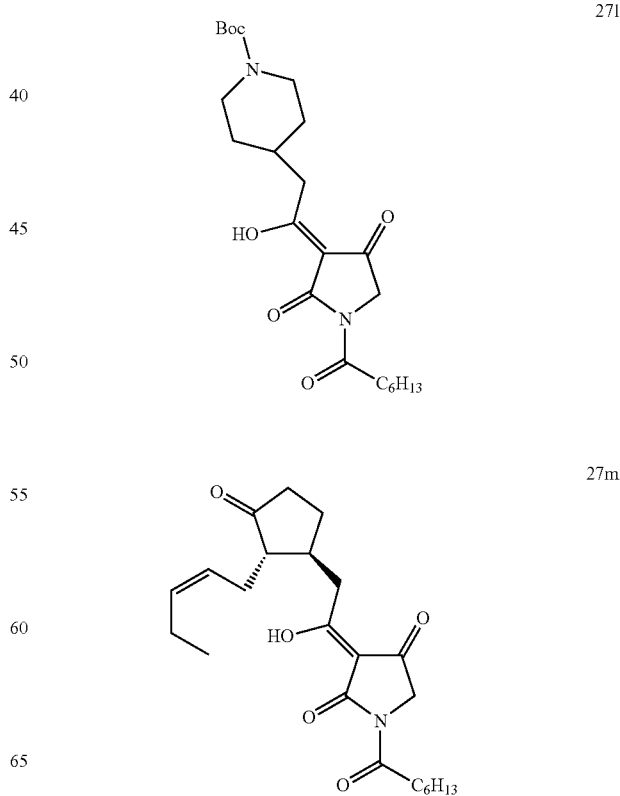

27l

27m

37
-continued
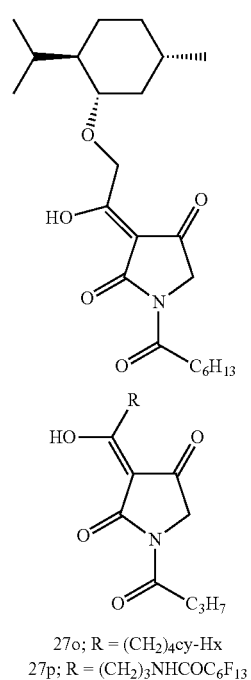
27o; R = (CH₂)₄cy-Hx
27p; R = (CH₂)₃NHCOC₆F₁₃
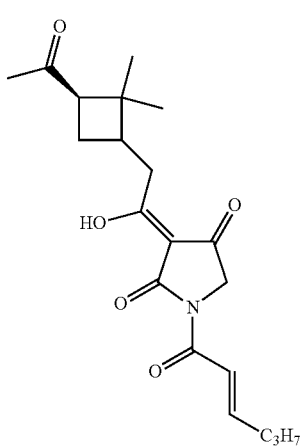
27q
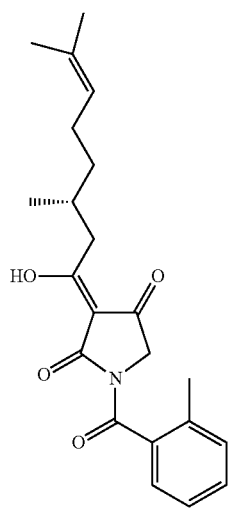
27r
38
-continued
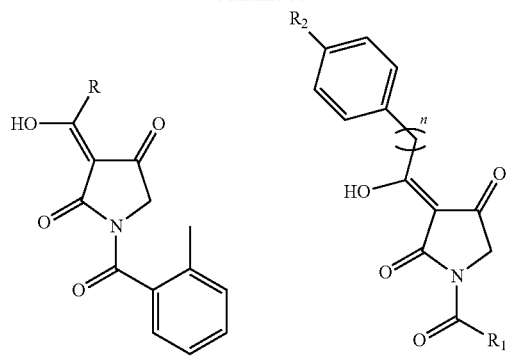
27s; R = (CH₂)₄cy-Hx
27t; R = C₄H₉CH=CH₂
27u; R = trans-CH₂CH=CHC₂H₅
28a; R₁ = C₆H₁₃, R₂ = H, n = 0
28b; R₁ = C₆H₁₃, R₂ = H, n = 4
28c; R₁ = C₆H₁₃, R₂ = SMe, n = 0
28d; R₁ = C₆H₁₃, R₂ = SMe, n = 2
28e; R₁ = C₃H₇, R₂ = H, n = 4
28f; R₁ = C₃H₇, R₂ = SMe, n = 2
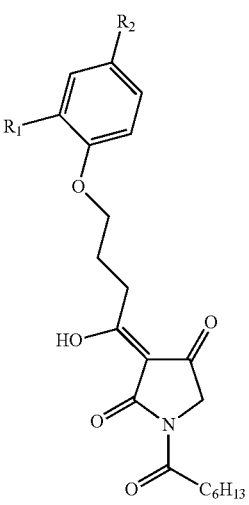
28g; R₁ = R₂ = H
28h; R₁ = Me, R₂ = Cl
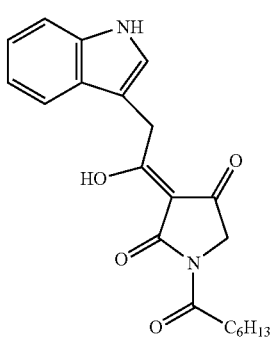
28i 28j
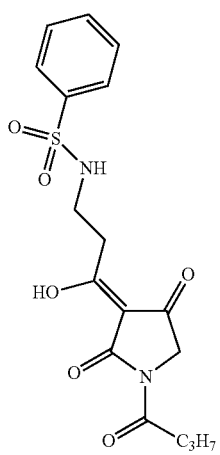
29a
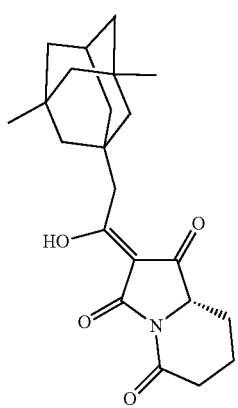
29b
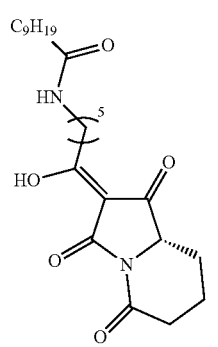
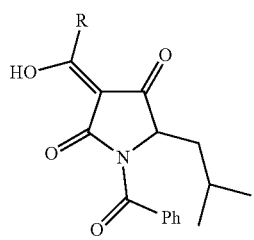
30a; R = (CH₂)₅Ph
30b; R = (CH₂)₃OPh
30c
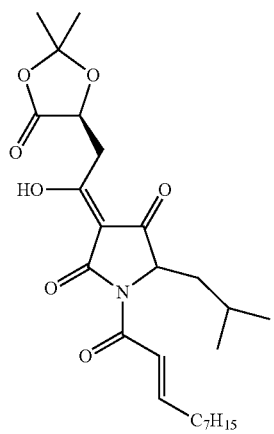
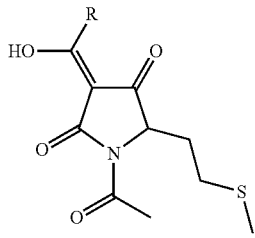
31a; R = (CH₂)₄cy-Hx
31b; R = (CH₂)₅NHCOC₉H₁₉
31c; R = CH₂CH(Me)CH₂C(Me)₃
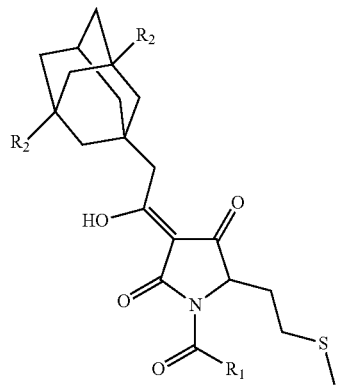
31d; R₁ = Me, R₂ = H
31e; R₁ = Me, R₂ = Me
31f; R₁ = cy-Hx, R₂ = H
31g
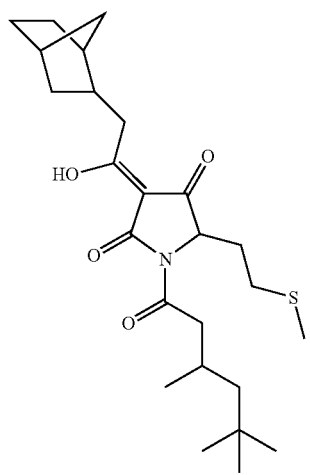

31h
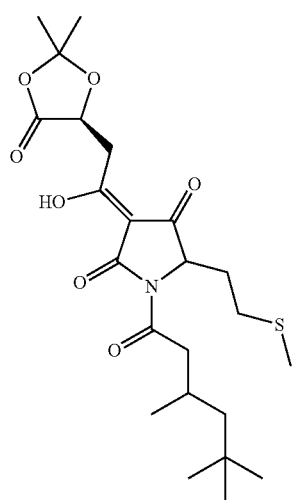
31i
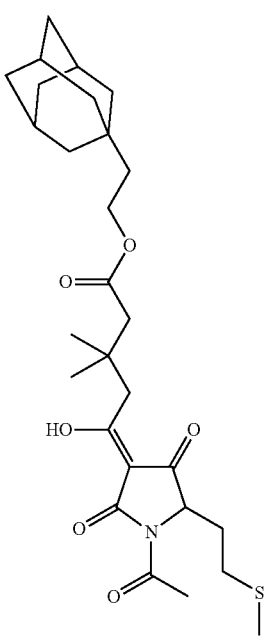
31j
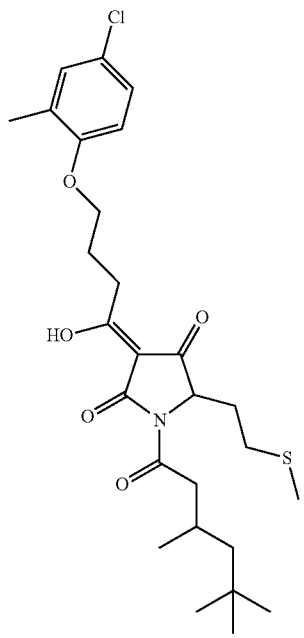
19a
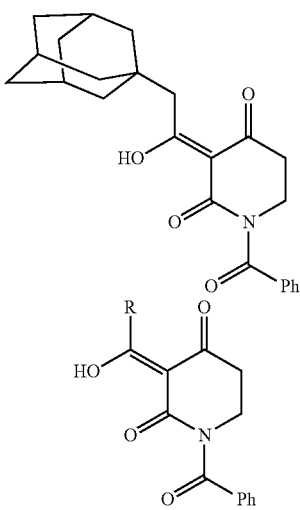
19b; R = CH₂C(Me)₃
19c; R = (CH₂)₄cy-Hx
19d
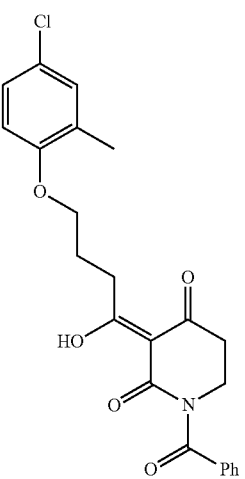

-continued

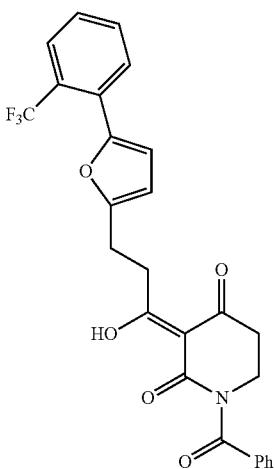

19e

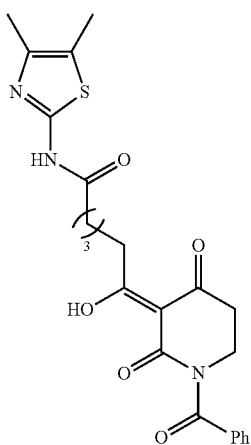

19f

MIC determination (bacteria); MICs were determined based on Clinical and Laboratory Standards Institute (CLSI) methodology (Methods for dilution antimicrobial susceptibility tests for bacteria that grow aerobically; Approved Standard—seventh edition. 2006, M7-A7, CLSI, Wayne Pa.) by a 2-fold broth dilution technique in Mueller Hinton (pH7.4 Biorad). For *S. pneumoniae*, the medium was supplemented with 2.5% laked horse blood. For *H. influenzae*, the medium was *haemophilus* test medium (H.T.M.). Overnight cultures were diluted to obtain the final inoculum of 105 cfu/well. Incubation was 37° C. overnight in ambient air. The MIC was defined as the lowest concentration which inhibited all visual growth and expressed in µg/ml. For each bacterial species, all of the molecules were tested in the same experiment in order to give a head-to-head comparison. The results are shown in the Tables 1 and 2 below:

MIC determination (fungus); MICs were determined for the antifungus by microdilution methods using RPMI 1640 medium buffered with morpholinopropanesulfonic acid (MOPS) and supplemented with L-glutamine as described by CLSI procedures (M27-A method) (Reference method for broth dilution antifungal susceptibility testing of yeasts; Approved standard—third edition. 2006, M27-A2, CLSI, Wayne Pa.). After incubation for 24-48 hours at 35° C., the lowest concentration of drug which produced 80% reduction in visible growth compared with control was considered as the MIC. The results are shown in the Tables 1 and 2 below.

The pharmacological properties of these derivatives were also determined and the results are shown in Table 3 below. These properties can be determined according to techniques that are well known in the art.

TABLE 1

In vitro antibiotic activity (MIC, µg/mL) of 3-acyl analogues 21-25.

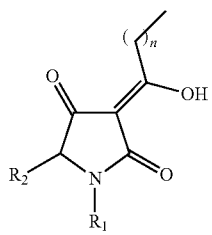

3ATs 20-24

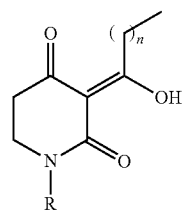

3APs 25

| | | | | | Antibacterial strains | | | | | | | |
|---|---|---|---|---|---|---|---|---|---|---|---|---|
| no | n + 1 | S1 | S26 | S4 | S2 | E1 | E2 | P1 | P9 | P9B | H3 | H4 |
| 21a | 9 | 2 | 8 | 8 | 4 | 1 | 2 | 1 | 1 | 4 | 8 | 2 |
| 21b | 11 | 0.25 | 2 | 1 | 1 | 0.25 | 0.5 | <0.06 | 0.12 | 2 | 4 | 2 |
| 21c | 13 | 0.25 | 16 | 4 | 1 | 2 | <0.06 | 0.12 | <0.06 | 1 | >64 | 4 |
| 21d | 4 | 32 | 32 | 32 | 32 | 16 | 16 | 8 | 4 | 8 | 4 | 1 |
| 21e | 6 | 1 | 8 | 8 | 4 | 2 | 2 | 1 | 1 | 4 | 8 | 2 |
| 21f | 11 | 8 | 8 | —d | 8 | 8 | 0.12 | 2 | —c | —c | >64 | —c |
| 21g | 13 | 64 | 64 | —d | 64 | 8 | 1 | 2 | —c | —c | >64 | —c |
| 21h | 9 | 0.5 | 2 | 2 | 2 | 1 | 1 | 0.5 | 0.25 | 4 | >64 | 16 |
| 21i | 11 | 2 | 8 | 4 | 4 | 4 | 0.5 | 1 | 1 | 8 | >64 | >64 |
| 21j | 8 | 32 | 32 | 32 | 32 | 32 | 16 | 4 | 4 | 8 | 32 | 8 |
| 21k | 10 | 2 | 8 | 8 | 4 | 2 | 2 | 1 | 0.5 | 2 | 32 | 4 |

TABLE 1-continued

In vitro antibiotic activity (MIC, μg/mL) of 3-acyl analogues 21-25.

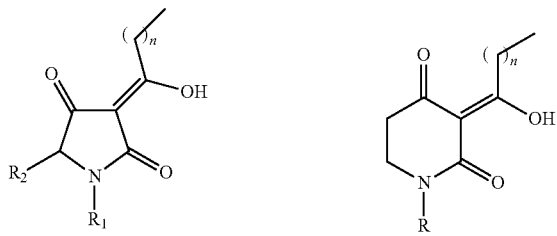

3ATs 20-24　　　　3APs 25

| no | n + 1 | S1 | S26 | S4 | S2 | E1 | E2 | P1 | P9 | P9B | H3 | H4 |
|---|---|---|---|---|---|---|---|---|---|---|---|---|
| 23a | 1 | 8 | 16 | 8 | 8 | 8 | 4 | 2 | 1 | 4 | 64 | 4 |
| 23b | 3 | <0.06 | 0.5 | 0.25 | 0.25 | 0.25 | <0.06 | 0.25 | 0.12 | 1 | >64 | 2 |
| 23c | 5 | 0.25 | 0.5 | 0.5 | 0.5 | 0.25 | 0.12 | <0.06 | <0.06 | 2 | >64 | —$^c$ |
| 24a | 10 | 0.5 | 8 | 4 | 2 | 0.5 | 0.5 | 0.5 | 0.25 | 2 | 8 | 4 |
| 24b | 11 | 0.25 | 2 | 1 | 1 | <0.06 | <0.06 | <0.06 | <0.06 | 0.5 | 2 | 2 |
| 24c | 12 | 0.5 | 4 | 2 | 2 | 0.12 | 0.25 | <0.06 | <0.06 | 2 | >64 | 8 |
| 24d | 5 | 2 | 4 | 2 | 4 | 2 | 2 | 2 | 2 | 4 | 32 | 4 |
| 24e | 7 | 0.5 | 1 | 2 | 0.5 | 0.25 | 0.5 | 0.12 | 0.12 | 1 | 16 | 2 |
| 24i | 5 | 0.25 | 1 | 0.5 | 0.5 | 0.5 | 0.25 | 0.25 | 0.25 | 2 | 8 | 2 |
| 24j | 7 | 0.5 | 1 | 0.5 | 0.5 | 0.25 | 0.25 | 0.12 | 0.12 | 4 | >64 | 2 |
| 24k | 9 | 0.5 | 1 | 0.5 | 0.5 | 0.5 | 0.25 | 0.25 | 0.12 | 2 | >64 | 64 |
| 24l | 7 | 4 | 8 | 8 | 8 | 8 | 2 | 1 | 1 | 4 | 8 | 2 |
| 24m | 9 | 2 | 4 | 2 | 2 | 2 | 0.5 | 0.5 | 0.25 | 4 | 16 | 4 |
| 25a | 9 | 2 | 4 | 2 | 4 | 2 | 4 | 0.5 | 0.5 | 4 | 16 | 8 |
| 25b | 11 | 0.5 | 1 | 0.5 | 0.5 | 0.25 | 0.5 | 0.25 | 0.25 | 1 | 8 | 4 |
| 25c | 13 | 2 | 4 | 1 | 2 | 2 | 1 | 1 | 1 | 8 | >64 | 32 |
| 25d | 9 | 8 | 8 | 4 | 4 | 4 | 4 | 2 | 2 | 8 | 64 | 8 |
| 25e | 11 | 4 | 4 | 1 | 4 | 1 | 1 | 0.5 | 0.5 | 8 | >64 | 8 |

TABLE 2

In vitro antibiotic activity (MIC, μg/mL) of 3-acyl analogues 19 and 26-31.

|  | S1 | S26 | S4 | S2 | E1 | E2 | P1 | P9 | P9B | H3 | H4 |
|---|---|---|---|---|---|---|---|---|---|---|---|
| 27a | 1 | 4 | 2 | 2 | 1 | 2 | 1 | 0.5 | 4 | 4 | 1 |
| 27b | 2 | 4 | 4 | 4 | 2 | 2 | 1 | 0.5 | 2 | 4 | 0.5 |
| 27c | 0.25 | 1 | 0.5 | 1 | 0.5 | 0.12 | 0.12 | <0.06 | 2 | 2 | 1 |
| 27h | 0.25 | 0.5 | 0.5 | 0.5 | 0.25 | 0.25 | <0.06 | <0.06 | 1 | 2 | 2 |
| 27i | 0.25 | 0.5 | 0.25 | 0.25 | 0.12 | 0.25 | 0.12 | 0.12 | 1 | 2 | 1 |
| 27j | 16 | 16 | 16 | 16 | 8 | 8 | 4 | 4 | 4 | 16 | 4 |
| 27k | 2 | 2 | 2 | 2 | 0.5 | 1 | 1 | 0.5 | 1 | 8 | 4 |
| 27n | >64 | >64 | >64 | >64 | 8 | 2 | 0.5 | 0.5 | 8 | >64 | 2 |
| 27o | 4 | 8 | 16 | 4 | 4 | 2 | 0.5 | 0.5 | 4 | 8 | 2 |
| 27s | 16 | 16 | 16 | 16 | 8 | 8 | 2 | 2 | 16 | 32 | 4 |
| 28b | 2 | 4 | 2 | 2 | 2 | 1 | 0.5 | 0.25 | 2 | 8 | 2 |
| 28d | 4 | 32 | 16 | 8 | 1 | 2 | 0.5 | 0.5 | 4 | 4 | 1 |
| 28h | 1 | 4 | 4 | 2 | 0.5 | 0.5 | 0.5 | 0.5 | 4 | 8 | 4 |
| 30a | 2 | 4 | 2 | 2 | 2 | 2 | 1 | 1 | 4 | >64 | 8 |
| 31d | 16 | 32 | 16 | 32 | 16 | 16 | 8 | 8 | 8 | 32 | 4 |
| 31e | 2 | 1 | 4 | 4 | 4 | 4 | 2 | 2 | 4 | 32 | 4 |
| 31f | 0.5 | 1 | 0.5 | 2 | 0.5 | 1 | 1 | 0.5 | 2 | 32 | 2 |
| 31g | 0.12 | 0.5 | 0.5 | 0.5 | 0.25 | 0.25 | 0.5 | 0.25 | 2 | 32 | 2 |
| 31i | 8 | >64 | 16 | 8 | 2 | 1 | 2 | 2 | 4 | >64 | 8 |
| 31j | 0.5 | 1 | 1 | 0.5 | 1 | 0.25 | 0.5 | 0.25 | 8 | >64 | 8 |
| 19c | 1 | 2 | 2 | 2 | 2 | 1 | 1 | 1 | 4 | 16 | 8 |
| 19d | 2 | 4 | 4 | 4 | 4 | 4 | 2 | 1 | 4 | 16 | 8 |
| 19e | 4 | 4 | 4 | 4 | 2 | 2 | 2 | 2 | 8 | >64 | 16 | a-d; see foot note in Table 3, e; Analogues 27d,e,g,p,t,u, 28j, 29b, 30b,c and 31h had MIC >32 μg/ml for all strains.

f; Analogues 27f,q (MIC; 32 μg/ml), 28a, 29a and 19b,f (MIC; 16 μg/ml) were active against H4, had MIC >32 μg/ml against the other strains.

TABLE 3

Pharmacological properties of selected tetramic acids

| | RNAP[a,b] (IC$_{50}$, μM) | DEP[a] (IC$_{50}$, μM) | RBCL[a] (IC$_{50}$, μM) | Hek293[a] (LD$_{50}$, μM) | PMBC[a] (LD$_{50}$, μM) | SI[a] | SOL[a] (μM) | PPB[a] (%) |
|---|---|---|---|---|---|---|---|---|
| 21b | —[c] | —[c] | —[c] | 30.3 | 90.9 | 11 | >300 | 99.9 |
| 21e | —[c] | >100 | —[c] | 90.9 | 90.9 | 7.3 | —[c] | —[c] |
| 21f | —[c] | >100 | Inactive[d] | 30.3 | 30.3 | 1.5 | —[c] | —[c] |
| 21g | —[c] | >100 | Inactive[d] | >90.9 | 10.1 | <0.06 | —[c] | —[c] |
| 21i | —[c] | >100 | Active[d] | 30.3 | 90.9 | 2.9 | —[c] | —[c] |
| 22b | >100 | >100 | Active | 90.9 | >90.9 | 8.6 | 38-75 | —[c] |
| 23a | —[c] | 88.0[e] | Inactive[d] | 90.9 | 90.9 | 4.0 | —[c] | —[c] |
| 23b | —[c] | 49.5 | Inactive[d] | 90.9 | 90.9 | 137 | —[c] | —[c] |
| 23c | —[c] | 19.6 | Inactive[d] | 30.3 | 30.3 | 25 | —[c] | —[c] |
| 24b | 25 | —[c] | —[c] | 30.3 | 90.9 | 12 | >300 | 93.6 |
| 24c | —[c] | >100 | Active | 30.3 | 30.3 | 6.2 | >300 | 99.9 |
| 24e | —[c] | >100 | Inactive[d] | >90.9 | >90.9 | >75 | >300 | —[c] |
| 24i | 33 | >100 | Active | 10.1 | 30.3 | <8.3 | >300 | 100 |
| 24j | 19 | >100 | Active | 10.1 | 30.3 | <8.9 | >300 | 100 |
| 24k | —[c] | 68.8 | Active | 10.1 | 90.9 | <9.5 | >300 | —[c] |
| 24m | —[c] | >100 | Active | 30.3 | 90.9 | 6.9 | >300 | —[c] |
| 25a | >100 | 83.6 | Inactive[d] | >90.9 | >90.9 | >8.4 | >300 | 98.9 |
| 25b | 86 | 94.4 | Inactive[d] | >90.9 | >90.9 | >73 | >300 | —[c] |
| 25d | —[c] | 69.0 | Active | 90.9 | 90.9 | 9.1 | 150-300 | —[c] |
| 25e | —[c] | >100 | Active | 90.9 | 90.9 | 9.8 | 19-38 | —[c] |
| 26d | —[c] | >100 | Inactive[d] | >90.9 | 90.9 | 3.3 | —[c] | —[c] |
| 27a | —[c] | >100 | Inactive[d] | 90.9 | 90.9 | 16 | —[c] | —[c] |
| 27c | >100 | >100 | —[c] | 30.3 | 90.9 | 11 | >200 | 100 |
| 27h | >100 | —[c] | —[c] | 30.3 | 90.9 | 21 | 150-300 | 91.9 |
| 27i | 3.1 | >100 | Active | 10.1 | 30.3 | <16 | 67-200 | 99.9 |
| 27k | 6.7 | >100 | Active | 30.3 | 90.9 | 5.7 | >300 | —[c] |
| 28h | 33 | —[c] | —[c] | 30.3 | 90.9 | 6.4 | >300 | 100 |
| 30a | —[c] | >100 | Inactive[d] | >90.9 | 90.9 | 19 | >300 | —[c] |
| 31e | 11 | 91.4 | Active | 30.3 | 90.9 | 3.2 | >300 | —[c] |
| 31f | 40 | >100 | Inactive[d] | 90.9 | >90.9 | 21 | >300 | —[c] |
| 31g | >100 | >100 | Active | 10.1 | 30.3 | <9.1 | >300 | —[c] |
| 31j | 91 | >100 | Active | 10.1 | 30.3 | <11 | >300 | —[c] |
| 19d | —[c] | —[c] | —[c] | 90.9 | 90.9 | 9.7 | >300 | —[c] |

[a]; Abbreviation; RNAP; In vitro activity against *E. Coli* RNAP, DEP; In vitro activity in depolarization of *S. aureus* membrane, RBCL; In vitro mammalian red blood cell membrane lysis activity, CAN; In vitro antifungal activity against *Candida albicans*, Hek293; in vitro toxicities against human embryonic kidney 293 cells, PMBC; in vitro toxicities human peripheral blood cells, SI; Selectivity index; LD$_{50}$ of one of lower value between Hek293 and PMBC divided by MIC against *S. aureus* 2, MRSA in vivo after converting the unit of LD$_{50}$ from μM to μg/mL, SOL; aqueous solubility at pH 7.4 (water with 2% DMSO), PPB; ratio of plasma protein binding,
[b]; In vitro activity against RNAP (IC$_{50}$) of analogues 24a (16 μM), 28c (>100 μM), 28g (>100 μM), 29a (>100 μM), 30c (85 μM), 31b (34 μM), 31d (>100 μM), and streptolydigin (1e, 38 μM) and In vitro activity against *S. pneumonia* UPPS (IC$_{50}$) of analogues 25b (0.6 μM), 27i (0.4 μM) and 28g (>10 μM) were evaluated,
[c]; Not determined,
[d]; Active or inactive at 100 μM,
f; Not determined because of inactivity against *S. aureus* 2.

The invention claimed is:

1. An antibacterial composition comprising a compound or a pharmaceutically acceptable salt thereof, said composition optionally being a topical antibacterial composition; wherein the compound is of the Formula I or II below:

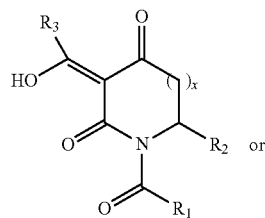

Formula I

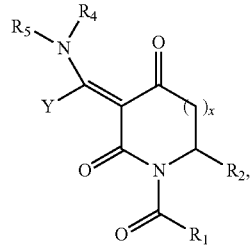

Formula II wherein
x is 0 or 1,
Y is OH or $C_1$ to $C_{15}$ alkyl,
$R_4$ is H or $C_1$ to $C_6$ alkyl,
either
$R_1$ is a $C_1$ to $C_{15}$ hydrocarbyl optionally substituted with a heterocyclic group or an ether group, and $R_2$ is H, ether, thioether or $C_1$ to $C_8$ alkyl, or $R_1$ and $R_2$ together form part of a 5-membered or 6-membered ring fused to the pyrrolidine/piperidine ring, $R_3$ and $R_5$ are each independently selected from a group of the formula $L_1$-$L_2$-$R_6$ or $L_2$-$L_1$-$R_6$, where $L_1$ is a linker of the formula —$[CR_8R_9]_n$—, where n is an integer of from 0 to 12, and $R_8$ and $R_9$ are in each instance each independently selected from H or $C_1$ to $C_2$ alkyl, and where $L_2$ is absent or a linker that is selected from O, S, SO, $SO_2$, N(R'), C(O), C(O)O, $[O(CH_2)_r]_s$, $[(CH_2)_rO]_s$, OC(O), CH(OR'), C(O)N(R'), N(R')C(O), N(R')C(O)N(R'), $SO_2N(R')$ or $N(R')SO_2$, where R' and R" are each independently selected from hydrogen and a $C_1$ to $C_2$ alkyl, and where r is 1 or 2 and s is 1 to 4, where $R_6$ is selected from $OR^{11}$, a heterocyclic and $C_1$ to $C_{25}$ hydrocarbyl group, wherein $R^{11}$ is a $C_1$ to $C_6$ alkyl, and wherein said heterocyclic and hydrocarbyl group is optionally substituted with at least one functional group selected from alkyl, alkenyl, aryl, halo, trihaloalkyl, alcohol, thio-alcohol, keto, S(O)$R^{11}$, ester, thioester, =O, =S, alkanoyl, ether, thio-ether, amide, thioamide, urea, thiourea, amine and heterocyclic group, with the proviso that the compound is not a compound of the formula III or IV below:

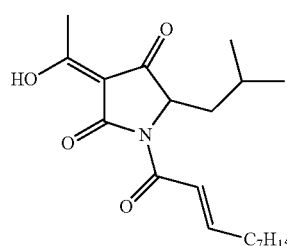

Formula III

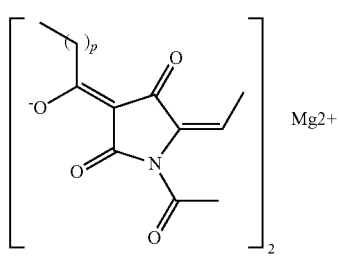

Formula IV wherein p is 2 or 4.

2. The composition as claimed in claim 1, wherein $R_1$ is selected from a $C_1$ to $C_{10}$ straight chain or branched alkyl or alkenyl group, or a phenyl group that is optionally substituted with a $C_1$ to $C_6$ alkyl.

3. The composition as claimed in claim 1, wherein $R_2$ is selected from hydrogen, a $C_1$ to $C_6$ alkyl or a thioether group of the formula $(CH_2)_qSR'$, where q is 1 to 4 and R' is a $C_1$ to $C_4$ alkyl group.

4. The composition as claimed in claim 1, wherein $L_1$ is absent or selected from $(CH_2)_n$ where n is 1 to 5, or $CH_2C(CH_3)_2CH_2$.

5. The composition as claimed in claim 1, wherein $L_2$ is selected from C(O)O, O(O)C, C(O)NH, HNC(O), NH, O and $O(C_2H_4)_2$.

6. The composition as claimed in claim 1, with the proviso that, when the compound is of Formula I and x=0, the following condition is not met: a) $R_3$ is methyl.

7. A method of using a compound or a pharmaceutically acceptable salt thereof as an antibacterial agent, wherein the compound is of the Formula I or II below:

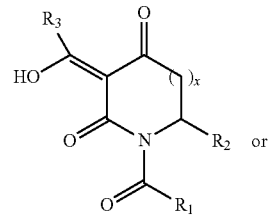

Formula I

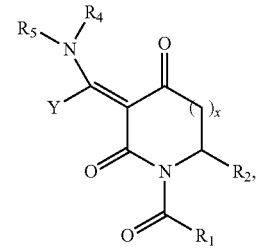

Formula II wherein x is 0 or 1,

Y is OH or $C_1$ to $C_{15}$ alkyl, $R_4$ is H or $C_1$ to $C_6$ alkyl, either $R_1$ is a $C_1$ to $C_{15}$ hydrocarbyl optionally substituted with a heterocyclic group or an ether group, and $R_2$ is H, ether, thioether or $C_1$ to $C_8$ alkyl, or $R_1$ and $R_2$ together form part of a 5-membered or 6-membered ring fused to the pyrrolidine/piperidine ring, $R_3$ and $R_5$ are each independently selected from a group of the formula $L_1$-$L_2$-$R_6$ or $L_2$-$L_1$-$R_6$, where $L_1$ is a linker of the formula —$[CR_8R_9]_n$—, where n is an integer of from 0 to 12, and $R_8$ and $R_9$ are in each instance each independently selected from H or $C_1$ to $C_2$ alkyl, and where $L_2$ is absent or a linker that is selected from O, S, SO, $SO_2$, N(R'), C(O), C(O)O, $[O(CH_2)_r]_s$, $[(CH_2)_rO]_s$, OC(O), CH(OR'), C(O)N(R'), N(R')C(O), N(R')C(O)N(R'), $SO_2N(R')$ or $N(R')SO_2$, where R' and R" are each independently selected from hydrogen and a $C_1$ to $C_2$ alkyl, and where r is 1 or 2 and s is 1 to 4, where $R_6$ is selected from $OR^{11}$, a heterocyclic and $C_1$ to $C_{25}$ hydrocarbyl group, wherein $R^{11}$ is a $C_1$ to $C_6$ alkyl, and wherein said heterocyclic and hydrocarbyl group is optionally substituted with at least one functional group selected from alkyl, alkenyl, aryl, halo, trihaloalkyl, alcohol, thio-alcohol, keto, S(O)$R^{11}$, ester, thioester, =O, =S, alkanoyl, ether, thio-ether, amide, thioamide, urea, thiourea, amine and heterocyclic group, with the proviso that the compound is not a compound of the formula III or IV below:

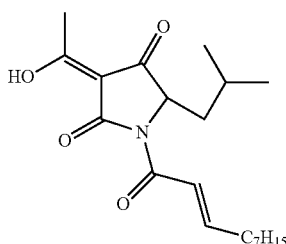

Formula III

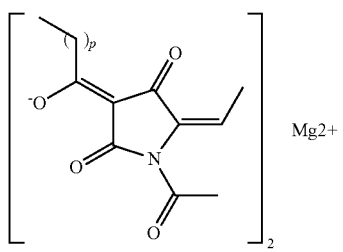

Formula IV wherein p is 2 or 4.

8. The method as claimed in claim 7, wherein the compound is used as a preservative.

9. The method as claimed in claim 7, wherein the compound is used in a non-edible composition.

10. The method as claimed in claim 9, wherein the compound is used in paper, fabric, building materials, packaging materials, coating and paint compositions, disinfectants, detergents, household products, cosmetics and suncreams.

11. A method of synthesising a compound of the Formula II,

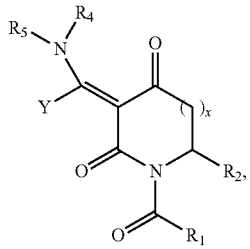

Formula II wherein
x is 0 or 1,
Y is OH or $C_1$ to $C_{15}$ alkyl,
$R_4$ is H or $C_1$ to $C_6$ alkyl,
either
$R_1$ is a $C_1$ to $C_{15}$ hydrocarbyl optionally substituted with a heterocyclic group or an ether group, and
$R_2$ is H, ether, thioether or $C_1$ to $C_8$ alkyl, or
$R_1$ and $R_2$ together form part of a 5-membered or 6-membered ring fused to the pyrrolidine/piperidine ring,
$R_5$ is selected from a group of the formula $L_1$-$L_2$-$R_6$ or $L_2$-$L_1$-$R_6$, where $L_1$ is a linker of the formula —$[CR_8R_9]_n$—, where n is an integer of from 0 to 12, and $R_8$ and $R_9$ are in each instance each independently selected from H or $C_1$ to $C_2$ alkyl, and where $L_2$ is absent or a linker that is selected from O, S, SO, $SO_2$, N(R'), C(O), C(O)O, $[O(CH_2)_r]_s$, $[(CH_2)_rO]_s$, OC(O), CH(OR'), C(O)N(R'), N(R')C(O), N(R')C(O)N(R'), $SO_2N(R')$ or $N(R')SO_2$, where R' and R" are each independently selected from hydrogen and a $C_1$ to $C_2$ alkyl, and where r is 1 or 2 and s is 1 to 4,
where $R_6$ is selected from $OR^{11}$, a heterocyclic and $C_1$ to $C_{25}$ hydrocarbyl group, wherein $R^{11}$ is a $C_1$ to $C_6$ alkyl, and wherein said heterocyclic and hydrocarbyl group is optionally substituted with at least one functional group selected from alkyl, alkenyl, aryl, halo, trihaloalkyl, alcohol, thio-alcohol, keto, S(O) $R^{11}$, ester, thioester, =O, =S, alkanoyl, ether, thio-ether, amide, thioamide, urea, thiourea, amine and heterocyclic group, the method comprises
reacting a compound of the formula V below

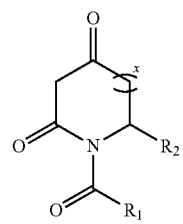

Formula V with a compound of the formula $R_5NCO$, or
reacting a compound of the formula VI below

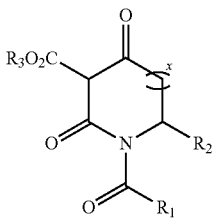

Formula VI with an amine of the formula $R_4R_5NH$, with the proviso that, where compound of the Formula V is reacted with $R_5NCO$, $R_4$ is H.

12. The method as claimed in claim 7, wherein $R_1$ is selected from a $C_1$ to $C_{10}$ straight chain or branched alkyl or alkenyl group, or a phenyl group that is optionally substituted with a $C_1$ to $C_6$ alkyl.

13. The method as claimed in claim 7, wherein $R_2$ is selected from hydrogen, a $C_1$ to $C_6$ alkyl or a thioether group of the formula $(CH_2)_qSR'$, where q is 1 to 4 and R' is a $C_1$ to $C_4$ alkyl group.

14. The method as claimed in claim 7, wherein $L_1$ is absent or selected from $(CH_2)_n$ where n is 1 to 5, or $CH_2C(CH_3)_2CH_2$.

15. The method as claimed in claim 7, wherein $L_2$ is selected from C(O)O, O(O)C, C(O)NH, HNC(O), NH, O and $O(C_2H_4)_2$.

16. The method as claimed in claim 7, with the proviso that, when the compound is of Formula I and x=0, the following condition is not met: a) $R_3$ is methyl.

* * * * *